(12) United States Patent
Salah et al.

(10) Patent No.: US 11,599,997 B2
(45) Date of Patent: *Mar. 7, 2023

(54) DENTAL IMAGING DEVICE

(71) Applicant: DENTAL MONITORING, Paris (FR)

(72) Inventors: Philippe Salah, Bagnolet (FR);
Laurent Debraux, Paris (FR); Thomas Pellissard, Clichy (FR); Guillaume Ghyselinck, Cantin (FR)

(73) Assignee: DENTAL MONITORING, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/951,401

(22) Filed: Nov. 18, 2020

(65) Prior Publication Data

US 2021/0192724 A1   Jun. 24, 2021

Related U.S. Application Data

(63) Continuation of application No. 16/921,545, filed on Jul. 6, 2020, which is a continuation-in-part of
(Continued)

(30) Foreign Application Priority Data

Apr. 19, 2017 (FR) .................................. 1753389
Apr. 19, 2017 (FR) .................................. 1753392
Oct. 10, 2017 (EP) .................................. 17306361

(51) Int. Cl.
*G06T 7/00* (2017.01)
*A61C 9/00* (2006.01)
*G06T 5/50* (2006.01)

(52) U.S. Cl.
CPC .......... *G06T 7/0012* (2013.01); *A61C 9/0053* (2013.01); *G06T 5/50* (2013.01); *G06T 2207/30036* (2013.01)

(58) Field of Classification Search
CPC ................. G06T 7/0012; G06T 5/50; G06T 2207/30036; A61C 9/0053
(Continued)

(56) References Cited

U.S. PATENT DOCUMENTS 3,385,188 A * 5/1968 Ellman .................... A61B 6/14
396/199
4,564,355 A   1/1986 Traiger et al.
(Continued)

FOREIGN PATENT DOCUMENTS

DE   102009017819 A1   10/2010
EP       0420715 A1    4/1991
(Continued)

OTHER PUBLICATIONS

"Dental Informatics and Intra-oral Photography in Communicating with Dental Students in the Dominican Republic"—Lawrence Parrish, Anton Diy, Nicholas R. Kenning, Kristen Templeton, Ruben Sagun, Nicole S. Kimmes, Gene Gaspard, Stephen J. Hess; Journal of Health Informatics in Developing Countries (Year: 2014).*
(Continued)

*Primary Examiner* — Mainul Hasan
(74) *Attorney, Agent, or Firm* — Ronald M. Kachmarik; Cooper Legal Group LLC

(57) ABSTRACT

A method to acquire dental images of a patient with a support defining a chamber that is in communication with an outside of said chamber via a first opening and via a second opening. The method includes the following steps: fixing a mobile phone in front of the second opening; positioning the first opening in front of a mouth of the patient; and acquiring at least one dental image by means of the mobile phone.

28 Claims, 6 Drawing Sheets

Related U.S. Application Data application No. 15/953,744, filed on Apr. 16, 2018, now Pat. No. 10,736,715.

(58) Field of Classification Search
USPC .......................................... 382/128; 433/37
See application file for complete search history.

(56) References Cited

U.S. PATENT DOCUMENTS

| | | | |
|---|---|---|---|
| 5,677,537 A * | 10/1997 | Pfeiffer | A61B 1/05 250/370.09 |
| 6,964,567 B2 * | 11/2005 | Kerschbaumer ... | A61B 1/00041 433/140 |
| 9,939,714 B1 * | 4/2018 | Matthews | H04N 5/2256 |
| 10,595,966 B2 * | 3/2020 | Carrier, Jr. | A61C 9/0053 |
| 10,932,885 B2 * | 3/2021 | Carrier, Jr. | A61C 9/0053 |
| 2004/0064019 A1 | 4/2004 | Chang et al. | |
| 2006/0040230 A1 | 2/2006 | Blanding et al. | |
| 2008/0032252 A1 | 2/2008 | Hayman et al. | |
| 2012/0040305 A1 * | 2/2012 | Karazivan | A61B 1/05 433/29 |
| 2013/0209954 A1 * | 8/2013 | Prakash | A61B 1/043 433/29 |
| 2014/0005484 A1 * | 1/2014 | Charles | A61B 50/13 600/201 |
| 2015/0234192 A1 * | 8/2015 | Lyons | G02B 27/022 345/8 |
| 2018/0000563 A1 * | 1/2018 | Shanjani | A61C 7/08 |
| 2018/0125610 A1 * | 5/2018 | Carrier, Jr. | A61C 9/0053 |
| 2018/0228359 A1 * | 8/2018 | Meyer | A61C 5/90 |
| 2019/0167115 A1 | 6/2019 | Dorodvand et al. | |
| 2020/0297205 A1 * | 9/2020 | Hill | A61B 1/04 |

FOREIGN PATENT DOCUMENTS

| | | |
|---|---|---|
| EP | 1252858 A2 | 10/2002 |
| EP | 1252859 A2 | 10/2002 |
| EP | 1477107 A1 | 11/2004 |
| FR | 3004098 A1 | 10/2014 |
| FR | 3027506 A1 | 4/2016 |
| JP | 2005168520 A | 6/2005 |
| WO | 2013151509 A1 | 10/2013 |
| WO | 2015016377 A1 | 2/2015 |
| WO | 2016066651 A1 | 5/2016 |
| WO | 2021058930 A1 | 4/2021 |

OTHER PUBLICATIONS

"Dental Informatics and Intra-oral Photography in Communicating with Dental Students in the Dominican Republic"—Lawrence Parrish et al., Journal of Health Informatics in Developing Countries; Apr. 30, 2014. (Year: 2014).*

"A 3-D Reconstruction System for the Human Jaw Using a Sequence of Optical Images"—Sameh M. Yamany, Aly A. Farag, David Tasman, Allan G. Farman; IEEE Transactions on Medical Imaging, vol. 19, No. 5, May 2000. (Year: 2000).*

"3-D Reconstruction of the Human Jaw Using Space Carving"—Moumen T. Ahmed, Ahmed H. Eid and Aly A. Farag; Computer Vision and Image Processing (CVIP) Laboratory, University of Louisville, Louisville, KY 40292; 0-7803-6725- 1/01/$10.00 C2001 IEEE. (Year: 2001).*

Corresponding French Application, French Search Report, Application No. 1753389, dated Jan. 3, 2018, 2 pages.

I. Ahmad: "Digital dental photography Part 8: intra-oral set-ups" BDJ, vol. 207, No. 4, Aug. 22, 2009 (Aug. 22, 2009), pp. 151-157, XP055209322, ISSN: 0007-0610, DOI:10.1038/sj.bdj.2009.715; Entire Document.

Corresponding French Application, French Search Report, Application No. 1753392, dated Jan. 3, 2018.

Corresponding European Application, Application No. 17306361.1, European Office action/ Search Report, dated May 14, 2018, 7 pages.

* cited by examiner

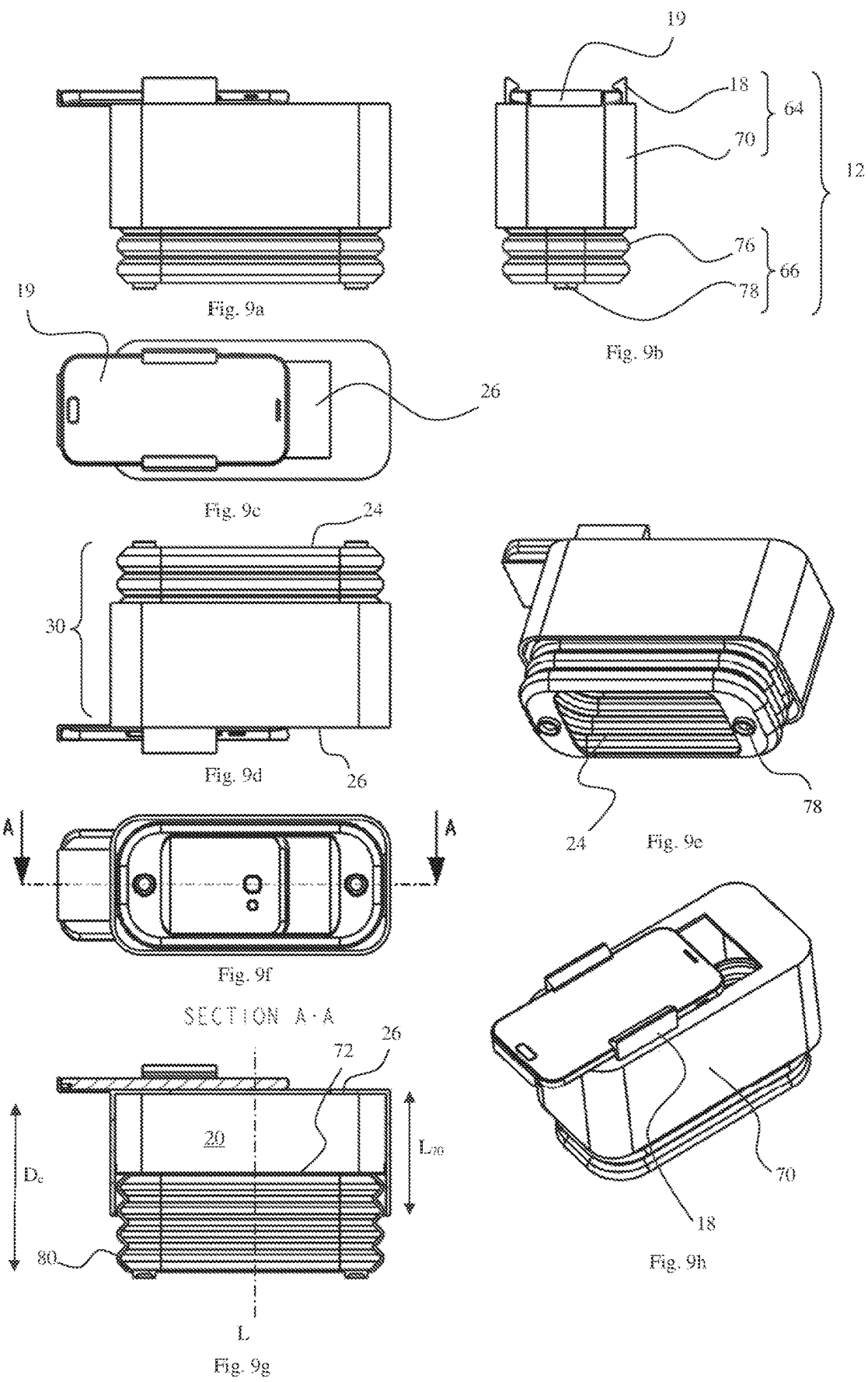

DENTAL IMAGING DEVICE

TECHNICAL FIELD

The present invention relates to a dental imaging device, in particular for implementing a method such as described in international application PCT/EP2015/074896.

PRIOR ART

PCT/EP2015/074896 describes a method allowing, on the basis of
- a three-dimensional model of the teeth of a patient produced before treatment, referred to as the "initial reference model"; then
- a simple "updated" image of the teeth taken during treatment, for example a photograph taken by the patient, the positioning of the teeth at the moment of acquisition of the updated image to be accurately evaluated.

This method consists in an iterative process in which, upon each iteration, models of teeth from the initial reference model are moved, then optimum conditions for observing the initial model thus modified (referred to as the "test reference model") are determined, the optimum observation conditions being defined as the conditions allowing the test reference model to be observed so that the view of said model is as close as possible to the updated image. A succession of "test reference models" are tested until obtaining a maximum level of correspondence between a test reference model and the updated image. This last test reference model is then considered to be representative of the teeth in their position at the moment of acquisition of the updated image. Ideally, this model, referred to as the "updated reference model", is a digital three-dimensional reference model from which the updated image could have been taken had this model been real. In practice, it actually represents, with a high level of accuracy, the teeth in their position at the moment of acquisition of the updated image.

Generally, multiple updated images are required to evaluate the positioning of multiple teeth. The method must be implemented for each updated image. The method described in international application PCT/EP2015/074896 may therefore be lengthy in its implementation.

Furthermore, the updated images may be used to detect variations in the appearance of the teeth or of the soft tissues such as the gums, and in particular in their color and in their translucence. Comparing various photos does not however always yield satisfactory results.

One object of the present invention is to provide an at least partial response to these problems.

SUMMARY OF THE INVENTION

The invention provides an imaging device including:
a support;
a dental retractor, fastened to the support, defining a retractor opening; and
means for fastening an image acquisition apparatus to the support in a position in which the acquisition apparatus is oriented so as to receive an image of the retractor opening.

As will become more clearly apparent throughout the rest of the description, a device according to the invention advantageously makes it possible to define a precise positioning of the image acquisition apparatus with respect to the dental retractor. In particular, the distance between the means for fastening the image acquisition apparatus and the dental retractor may be predetermined, thereby allowing the adjustment of the image acquisition apparatus to be accelerated. Furthermore, the orientation of the image acquisition apparatus with respect to the support may be predetermined, thereby making it possible to approximately predict the representation of the dental retractor, and, through the dental retractor, of the arches of the patient, on the updated images acquired by means of the image acquisition apparatus.

The later processing of the images, in particular according to the method of PCT/EP/2015/074896, is accelerated thereby.

According to a first main refinement, the device includes a mirror fastened to the support and said fastening means are configured to fasten the image acquisition apparatus to the support in a position in which the acquisition apparatus is oriented so as to receive a composite image including a direct image of the retractor opening and an image of the retractor opening reflected by the mirror.

In a service position in which the dental retractor is positioned on the mouth of the patient and the image acquisition apparatus is fastened to the support by said fastening means, said acquisition apparatus thus sees a composite image including a direct image of the teeth that is observed directly through the retractor opening and a reflected image of the teeth returned by the mirror.

As will become more clearly apparent later on in the description, a device according to the first main refinement of the invention thus allows multiple images of the teeth, observed from different angles, to be acquired simultaneously. The acquisition process is accelerated as a result.

In addition, determining the conditions for acquiring the direct image, or the reflected image, makes it possible to determine the conditions for acquiring the reflected image, or the direct image, respectively. It is in fact sufficient to have knowledge of the orientation of the mirror and its position with respect to the dental retractor and to the acquisition apparatus in order to determine the positioning in space of the acquisition apparatus which would have allowed, in the absence of the minor, the reflected image to be observed. The implementation of a method such as that in international application PCT/EP2015/074896 is consequently considerably accelerated as a result.

Specifically, typically, the patient takes a photo of his or her teeth from the right, a photo of his or her teeth from the left and a photo of his or her teeth from the front. However, the software implementing the method described in international application PCT/EP2015/074896 ignores the position of the acquisition apparatus in these various steps and is not able to deduce it by processing the other images. It must therefore find it again each time in order to define the optimum observation conditions.

According to a second main refinement, the device includes
a colorimetric calibration chart and/or a translucence calibration chart, preferably both a colorimetric calibration chart and a translucence calibration chart, preferably fastened to the support; and
preferably a light source that is oriented so as to illuminate both the teeth of the patient through the retractor opening and said colorimetric calibration chart and/or said translucence calibration chart, said fastening means of the acquisition apparatus being configured to immobilize the acquisition apparatus in a position in which it is oriented so as to receive an image of both the retractor opening and of said colorimetric calibration chart and/or of said translucence calibration chart.

As will become more clearly apparent later on in the description, a device according to the second main refinement of the invention thus allows the color and the translucence of the teeth and/or of the soft tissues, such as the gums, to be accurately determined. In particular, the illumination may be monitored so as to limit disruptions due to the lighting environment of the device. Various images taken at different times may therefore be accurately compared.

According to a third main refinement, the support takes the form of a box so as to define a chamber that is in communication with the outside substantially only via the retractor opening and via an acquisition opening through which the acquisition apparatus fastened to the support receives at least one image of the retractor opening.

Thus, the support defines a closed chamber when the opening of the dental retractor and the acquisition opening are obturated.

Advantageously, the inside of the chamber therefore receives substantially no luminous radiation from the outside, thereby facilitating the control of the illumination during the acquisition of updated images. A closed box also protects the patient's privacy.

In one embodiment, the dental retractor is mounted mobile, movably mounted, on the support, preferably rotatably mounted on the support, preferably around a single axis, preferably an horizontal axis in the service position, so that a gap between the support and the dental retractor occurs when the dental retractor is moved relative to the support. An obturator is provided to extended so as to obturate this gap. In particular, the obturator may have the shape of a flexible membrane, the edge of which is rigidly fixed on the dental retractor and on the support. Such a membrane may be elastic.

Advantageously, the flexibility and/or the elasticity of the membrane allows the membrane to obturate the gap between the support and the dental retractor, even if the dimensions of this gaps varies when the dental retractor is moved relative to the support.

Improvements

According to a first improvement, the imaging device has a support which comprises a rigid portion on which the acquisition apparatus is to be fastened to, and a deformable portion defining a retractor opening, preferably extending between the rigid portion and a conventional dental retractor.

The deformability of the deformable portion defining a retractor opening allows an adaptation of the imaging device to the patient. Consequently, the same support and dental retractor may be used for patients having different anatomies. Using the device is made more comfortable and the quality of the acquired images is improved.

The support is preferably in the form of a box, and has a lateral wall defining a chamber in communication with the outside via a retractor opening and an acquisition opening through which the acquisition apparatus fastened to the support receives at least one image of the retractor opening. The deformable portion is preferably at least a portion of the lateral wall of the support.

In an embodiment, the deformable portion enables limited movements of the rigid portion relative to the retractor opening, in particular so that the variation of the angle between the optical axis of the image acquisition apparatus and the retractor opening be limited to less than 30°, less than 20°, less than 10°, or less than 5°. This variation is preferably greater that 1° or 3°.

The rigid portion, preferably having a tubular shape, makes the fastening of the image acquisition apparatus easier. Preferably, its length is greater than 5 cm, and less than 20 cm, so that the patient may easily grab it to hold the support.

The deformable portion preferably allows an extension and/or a collapsing of the support.

Preferably, the deformable portion may be inserted, at least partly, into the rigid portion and extracted from said rigid portion. The imaging device may thereby be compacted.

In an embodiment, the deformable portion may be detached of the rigid portion. This advantageously makes shipment easier.

According to a second improvement, the support is extendable from a collapsed configuration to a fully extended configuration, and/or collapsible from said fully extended configuration to said collapsed configuration.

Put differently, at least one dimension of the support has a "collapsed" value $D_c$ in a collapsed configuration, and an "extended" value $D_e$, greater than the collapsed value $D_c$, in the fully extended configuration.

In a preferred embodiment, the support, preferably in the form of a box, has a lateral wall defining a chamber in communication with the outside via a retractor opening and an acquisition opening through which the acquisition apparatus fastened to the support receives at least one image of the retractor opening, said lateral wall being extendable and/or collapsible between a fully extended configuration and a collapsed configuration.

Said dimension is preferably an overall dimension of the chamber, preferably its length, and the ratio $D_c/D_e$ is preferably less than 0.5.

Advantageously, the bulk of the support is reduced in the collapsed configuration, so that storage and shipment costs are reduced.

Preferably, the support is configured so that, in the fully extended configuration and/or in an intermediate configuration between the collapsed and fully extended configurations, the angulation between an optical axis of the image acquisition apparatus and the retractor opening and/or the distance between the image acquisition apparatus and the retractor opening is (are) different than in the collapsed configuration.

Advantageously, the extension of the support therefore enables a modification of the acquisition conditions.

Preferably, the lateral wall is foldable. In particular, the lateral wall preferably comprises a bellow.

Preferably, the support is configured so that extension and/or collapsing of the support is fully or partly guided.

"Fully guidance" or "hard guidance" means that there is only one path of intermediate configurations between the collapsed configuration and a unique fully extended configuration.

"Partial guidance", or "soft guidance" means that several paths are possible between the collapsed configuration and a unique fully extended configuration or several fully extended configurations, each path enabling different deformations but some of these deformations requiring more efforts than other. The guidance is not hard since the patient has several possibilities to deform the support. However, the patient can feel that said deformations are not recommended.

Advantageously, the patient can therefore feel one or several privileged configurations from which greater efforts are necessary to go away.

The privileged configurations preferably correspond to predetermined acquisition conditions to acquire images according to predetermined angulations and/or distances.

For instance, after having fastened a mobile phone on the support, and having inserted the dental retractor into his mouth, the patient manipulates the mobile phone. When he pushes it to his right, he feels a first "angle" resistance when the optical axis of the mobile phone makes an angle of about 40° with the plane of the retractor opening. This informs the patient that this angle is appropriate to acquire an image.

When he pushes the mobile phone toward the retractor opening, he feels a first "distance" resistance when the distance between the mobile phone and the retractor opening is about 20 cm. This informs the patient that this distance is appropriate to acquire a first image.

The patient has then reached a first privileged configuration.

The patient may further push the mobile phone to his right and/or toward the retractor opening, by increasing the pushing force against said first resistances. Once he has left the first privileged configuration, the "angle" and "distance" resistances decrease. When the patient further pushes the mobile phone to his right, he may feel a second "angle" resistance when the optical axis of the mobile phone makes an angle of about 60° with the plane of the retractor opening. This informs the patient that this angle is appropriate to acquire an image. When he further pushes the mobile phone toward the retractor opening, he may feel a second "distance" resistance when the distance between the mobile phone and the retractor opening is about 10 cm. This informs the patient that this distance is appropriate to acquire a second image.

The patient has then reached a second privileged configuration.

According to a third improvement, at least a portion of the support is degradable by composting and/or biodegradation, preferably according to the European standard EN 13432, preferably with a residue of less than 10%, preferably less than 5%, preferably less 1% in 6 months.

Said portion is preferably made in a fibrous cellulosic material, preferably in cardboard.

Preferably, more than 50%, 70%, 80%, or 90% of the support, in percentage by weight, is so degradable.

In a preferred embodiment, the support, preferably in the form of a box, has a lateral wall defining a chamber in communication with the outside via a retractor opening and an acquisition opening through which the acquisition apparatus fastened to the support receives at least one image of the retractor opening, said degradable portion including or being said lateral wall.

In an embodiment of the second and/or third improvements, the support carries the image acquisition apparatus, but does not define a retractor opening to be surrounded by the lips of the patient in the service position. A dental retractor, independent of the support, may be worn by the patient or not.

Of course, the features of the various main refinements of the invention and of the improvements may be combined (as far as the combined features are technically compatible).

Regardless of the main refinement or of the improvement under consideration, a device according to the invention preferably has one or more of the following optional features:
  the support defines a chamber that is in communication with the outside via the retractor opening and via an acquisition opening through which the acquisition apparatus fastened by said fastening means receives said composite image;
  the support is telescopic so that the distance between the retractor opening and acquisition opening is variable;
  the device includes at least two of said mirrors that are oriented perpendicularly to one another and each returning a reflected image of the retractor opening, each of said reflected images being represented in said composite image;
  the means for fastening the acquisition apparatus to the support can be deactivated;
  the means for fastening the acquisition apparatus and/or the dental retractor to the support are chosen from the group consisting of a clip fastener, a self-gripping strip, clamping jaws, a screw, a magnet, a cover, a complimentary shape between the support and the acquisition apparatus, and an elastic member;
  the device includes means for fastening the dental retractor to the support, which means can be deactivated, the dental retractor thus being able to be removably fastened to the support;
  the dental retractor includes tabs which, in a position in which the dental retractor is mounted on the support, are inserted into respective profiled compartments of the support, each compartment having a generally U-shaped cross section, the opening of the U preferably facing upward or downward in a service position in which the dental retractor is positioned on the mouth of a patient holding his or her head vertically;
  in said mounted position, the dental retractor is kept flexed, bearing elastically on the support;
  the support includes one or more, preferably two, hooks configured to accommodate the dental retractor in said mounted position;
  the light source is configured so as to project a reference frame toward the retractor opening;
  the device includes a monitoring module configured to monitor the properties of the radiation emitted by the light source, preferably as a function of the luminous radiation received by the retractor opening;
  the monitoring module is configured to control the light source so that more than 50%, more than 70%, more than 90%, or even substantially 100% of the intensity of the radiation received by the retractor opening comes from the light source;
  the device includes a processing module in which the colour and translucence properties of the colorimetric and translucence calibration charts are recorded, respectively, the processing module comprising program code instructions for correcting an image representing said calibration charts so that the representations of said calibration charts on the image have said color and translucence properties;
  the support is made in a fibrous material, preferably a cellulosic material;
  the support carries information, preferably guiding information to guide the patient during the acquisition of images and/or advertising information.
The invention also relates to:
a computer program, or "app" and in particular a specialized mobile phone app, comprising program code instructions for guiding imaging, and in particular, preferably, for
  specifying to an operator the number of updated images to be acquired, and/or
  guiding an operator to position the image acquisition apparatus in a predetermined position relative to the retractor opening, for instance to take a photo "from the right side", and/or
  guiding an operator to position his teeth in a predetermined position relative to the image acquisition apparatus, for instance to take a photo "from the right side", in particular when the image acquisition apparatus is immobile relative to the ground, and/or guiding an operator during an adjustment to the geometry of the support and/or when orienting the mirror and/or when positioning the mouth of the patient on the dental retractor, and/or controlling one or more actuators that are capable of modifying said geometry, in particular modifying the length of the support, and/or said orientation of the mirror;

a computer medium on which such a program is recorded, for example a memory or a CD-ROM; and a personal device, in particular mobile phone or a tablet, on which such a program is loaded.

The computer program may, in particular, use a neural network, and generally artificial intelligence.

The invention also relates to an imaging kit including:

an imaging device according to the invention; and an image acquisition apparatus fastened to the device in a position in which the acquisition apparatus is oriented so as to receive an image of patient's teeth, preferably an image of the dental opening defined by the imaging device, preferably an image of the retractor opening of a conventional dental retractor, preferably fastened on the support of the imaging device.

According to the first main refinement of the invention, the image acquisition apparatus may thus acquire said composite image.

A kit according to the invention preferably has one or more of the following optional features:

the acquisition apparatus is a mobile phone;

the mobile phone is fastened to the device in a position in which a front camera of the mobile phone, i.e. a camera on the same side of the mobile phone as the display screen of the mobile phone, receives an image of a retractor opening of an imaging device, and in particular an image of the dental retractor fastened on the support of the imaging device;

the support comprises at least a slider on which the image acquisition apparatus, preferably a mobile phone, is fastened to, said slider preferably allowing for the sliding of the image acquisition apparatus along at least one sliding direction in a plane perpendicular to the optical axis of the image acquisition apparatus;

the support comprises at least a first slider and a second slider on which the image acquisition apparatus, preferably a mobile phone, is fastened to, said first and second sliders allowing for the sliding of the image acquisition apparatus along first and second sliding directions, respectively, in a plane perpendicular to the optical axis of the image acquisition apparatus;

the image acquisition apparatus includes a computer program according to the invention;

the image acquisition apparatus is configured to take multiple photographs in succession, with different focal lengths, as a result of a single trigger action.

In one preferred embodiment, the imaging device includes a detection member and the image acquisition apparatus includes a detector for detecting the detection member that is configured so as to detect the detection member when the detection member is less than 20 cm, preferably less than 10 cm, preferably less than 5 cm and/or preferably more than 1 cm from the imaging device.

Preferably, the detector for detecting a detection member is configured so as to detect the detection member only when the detection member is less than 100 cm, preferably less than 50 cm, preferably less than 30 cm, preferably less than 20 cm, preferably less than 10 cm, preferably less than 5 cm from the imaging device.

As will become more clearly apparent throughout the rest of the description, such an imaging kit advantageously allows the image acquisition apparatus to react to the approach of the imaging device, and in particular to launch a computer program that is capable of guiding said imaging.

The present invention also refers to a method to manufacture a support of a device according to the invention, and optionally a dental retractor of a device according to the invention, said method comprising the following steps:

A) manufacturing of a precursor of the support, and optionally of the dental retractor, in a first place, and providing said precursor to an operator, preferably to a patient or an orthodontist, in a second place away from the first place, the distance between the first place and the second place being preferably greater than 1 km and/or less than 20 000 km;

B) transformation of said precursor into said support, and optionally into said dental retractor.

In an embodiment, at step A), the precursor is in a cellulosic material and has the shape of at least a sheet, preferably is a sheet of cardboard, the thickness of which being preferably less than 6 mm and greater than 0.5 mm, said precursor preferably representing folding lines and/or cutting lines and/or comprising tearable weakening lines.

If said precursor represents folding lines and/or cutting lines and/or comprising tearable weakening lines, at step B), the operator cuts the precursor along said cutting lines, and/or folds the precursor along said folding lines, and/or tears the precursor along said weakening lines, and/or rigidly fixes different parts of the precursor on each other, by insertion of tabs, or lugs, into corresponding slots or with glue or with staples or clips or with a loops and hooks fasteners, as Velcro®.

In an embodiment, at step A), the precursor is a feedstock for a 3D-printer, preferably a printer enabling an additive manufacturing, and the operator is provided with a file to control said 3D printer to transform said feedstock into the support or a part of the support. At step B), the operator programs the 3D printer with said file so that the 3D printer manufactures the support or said part of the support.

In an embodiment, at step A), the precursor is a set of parts of the support and is provided to the operator by mail, and, at step B), the operator assembles said parts, manually or with a tool.

In an embodiment, at step A), the precursor is a support or a part of the support in a collapsed configuration and, at step B), the operator extends the support or said part of the support to a fully extended configuration.

Further Improvements

The invention also provides an imaging device comprising:

a support;

preferably a dental retractor, preferably independent of the support, i.e. not fastened to the support, defining a retractor opening; and means for immobilizing an image acquisition apparatus to the support.

In this embodiment, no dental retractor is necessarily fastened to the support. The support may be independent of the patient, i.e. the patient may move without any displacement of the support.

The support preferably takes the form of a stand to be placed on the ground or on a table, or to be rigidly fixed on a window glass or on a mirror.

In a preferred embodiment, the height of the support is changeable so that the altitude of the image acquisition apparatus relative to the ground may be modified so that it substantially faces the head, and preferably the mouth of the patient.

Preferably, the image acquisition apparatus rests on the support. Means for immobilizing the image acquisition apparatus to the support may be simple retaining means, like a rim or a hook.

The features of the various main refinements and improvements and of a kit of the invention may be combined with this imaging device.

Preferably, the image acquisition apparatus is a mobile phone. It preferably has a front camera, i.e. a camera on the same side of the mobile phone as the display screen of the mobile phone, and it is immobilized relative to the support so that the front camera faces the patient.

The scene which is observed by the front camera therefore appears on the display screen of the mobile phone, which is exposed toward the patient. The patient can therefore advantageously visualize this scene and optimize the angulation and/or the distance of the mobile phone to acquire images corresponding to his needs.

In a preferred embodiment, guiding information is provided on the display screen, so as to help the patient to position himself correctly. This information is preferably a reference displayed in a position on the display screen such that, when a part of the patient or a register mark of a reference frame added to the patient, in particular a conventional dental retractor, matches the reference on the display screen, for instance is superimposed or completes the reference on the display screen, the preview image is according to a predetermined viewing angle and/or a view at a predetermined distance, so that the image acquisition apparatus is positioned according to target acquisition conditions.

Preferably, the reference is chosen from a group consisting of
- a point,
- a geometrical shape,
- a colored zone, for instance of a same color as said register mark,
- a shape identical to a shape of said register mark or of said part of the patient,
- a shape complementing a shape of said register mark or of said part of the patient,
- a line intended to be aligned with the general direction of the join between the upper teeth and the lower teeth when the teeth are clamped by the patient,
- a vertical line intended to be aligned with the join between the two upper incisors,
- marks corresponding to the position of the eyes or taking the form of an outline in which the mouth or the face of the patient must be positioned,
- a two-dimensional digital model or a three-dimensional digital model of a human part, specific to the patient or not, preferably representing lips, a mouth or teeth, in particular a two-dimensional or a three-dimensional digital model of a dental arch, preferably a two-dimensional or a three-dimensional digital model of a dental arch or of the mouth or of the lips of the patient, and combinations of these references.

The invention also refers to a method to acquire an image with a kit according to the invention,
the image acquisition apparatus being preferably a mobile phone and having a front face comprising a display screen and preferably a front camera, and a back face, opposite to the front face and comprising a back camera, and the support of the imagine device, preferably in the form of a box, having a lateral wall defining a chamber in communication with the outside via a retractor opening and an acquisition opening through which the acquisition apparatus, after it has been fastened to the support, receives an image of the retractor opening.

According to a first embodiment, said method comprises the following steps:
a) the patient fastens said mobile phone so that the back camera of the mobile phone observes the retractor opening through the acquisition opening;
b) the patient put the lips of the patient around the retractor opening, so that patient's teeth are visible through said retractor opening;
c) preferably, the display screen provides guiding information and the patient observes the reflection of the display screen on a mirror and modifies, according to said guiding information, the position of the mobile phone to meet target acquisition conditions;
d) the patient acquires images with the mobile phone.

According to a second embodiment, said method comprises the following steps:
a') preferably, the patient immobilizes the support relative to the ground, preferably on a window glass or a mirror;
b') the patient immobilizes the mobile phone relative to the support, to immobilize it relative to the ground, preferably he places the mobile phone on the support, preferably so that the front camera of the mobile phone substantially faces the patient;
c') optionally, the patient puts his lips around the retractor opening, preferably defined by a dental retractor, or uses his fingers or a tool such as a spoon to put his lips apart, so that patient's teeth are visible;
d') preferably, the display screen provides guiding information and the patient observes the guiding information on the display screen;
e') the patient modifies, preferably according to said guiding information, the position of his head to meet target acquisition conditions, and in particular to reach a target position and a target orientation relative to the mobile phone; and
f') the patient acquires images with the mobile phone.

The target acquisition conditions preferably correspond to specific images to be acquired, for instance to images to be taken from the left, from the right or in face of the patient's teeth. They are predetermined and may be stored in the mobile phone or sent to the mobile phone.

Guiding the movement of the patient, the mobile phone being immobilized relative to the ground, rather than guiding the movement of the mobile phone makes it possible to use a very simple support.

The support may in particular be a simple casing, provided with one or several suction cups enabling the fixing on a glass panel. It may be a desk or a console.

It is preferably made of plastic and/or in a fibrous material, preferably in a cellulosic material such as cardboard. It may be sent to the patient by mail, or a template of the support may be sent to the patient by email, or made available to the patient on Internet.

In a preferred embodiment, at step b'), the patient modifies the altitude of the mobile phone relative to the ground so that it substantially faces the head, and preferably the mouth of the patient. Preferably, the patient modifies the height of the support to change the altitude of the mobile phone.

DEFINITIONS

A "main refinement of the invention" defines a particularly remarkable optional feature.

A "patient" is understood to mean any person for whom a device according to the invention may be implemented, whether this person is sick or not, or whether this person is currently being treated or not. A device according to the invention may be used for an animal other than a human being.

A "mobile phone" is a device weighing less than 500 g, provided with a sensor enabling it to capture images, capable of exchanging data with another device more than 500 km away from the mobile phone, and capable of displaying said data, and in particular said images.

The "support" is the part of the imaging device on which the image acquisition apparatus is fastened to or immobilized. A dental retractor intended to maintain the mouth of a patient at least partly opened may be fastened to the support or be integral with the support. The retractor opening is the opening defined by the dental retractor, through which patient's teeth may be observed by the image acquisition apparatus. Preferably, the support and the dental retractor define a chamber which opens outwardly through an acquisition opening and the retractor opening.

In the service position, the retractor opening faces the patient's teeth and is surrounded by the patient's lips. Whether the dental retractor is fastened to the support or integral with the support, it should be rigid enough to push the lips away from the teeth, so as to leave the patient's teeth visible through said retractor opening.

The dental retractor may be formed as an integral part of the support.

The dental retractor may be the terminal portion of a tube, preferably having a circular or oval section, or a ring. This tube may be a support. The dental retractor may be an edge of the lateral wall defining said chamber on the side of the mouth.

Preferably, the dental retractor comprises a rim arranged in such a way that the patient's lips may rest on it, in a retracted position. This rim may radially, the radiality being defined relatively to the axis of the retractor opening.

The dental retractor may be fastened, preferably rigidly, to the support by any means.

The angulation of the acquisition opening or of the image acquisition apparatus relative to the retractor opening is the angle between the axis of the acquisition opening or the optical axis of the image acquisition apparatus, respectively, and the plane of the retractor opening.

The distance between the acquisition opening and the retractor opening is the distance between their respective centres.

The axis L of a chamber defining a retractor opening and an acquisition opening is the line which extends in the centre of the chamber between the centres of the acquisition opening and of the retractor opening of said chamber. It defines the direction along which the length of the chamber is measured.

A "transversal plane" is a plane which is perpendicular to the axis L.

The width of the chamber is the largest overall dimension in a cross section of the chamber, i.e. in a section perpendicular to the axis L of the chamber.

The thickness of the chamber is the smallest overall dimension in a cross section of the chamber.

The "acquisition conditions" for acquiring an image of the teeth specify the position and the orientation in space of an image acquisition apparatus in relation to the teeth of the patient, and preferably the calibration of this image acquisition apparatus, in order to acquire, at the time of said acquisition, by direct observation, said image. The acquisition conditions for acquiring a reflected image therefore specify the position and orientation in space that the image acquisition apparatus would have had to have taken, in the absence of the mirror, in order to acquire the reflected image.

The "calibration" of an acquisition apparatus consists of the set of values of the calibration parameters. A "calibration parameter" is a parameter intrinsic to the acquisition apparatus (unlike its position and its orientation), the value of which influences the image acquired. For example, the aperture is a calibration parameter that modifies the depth of field. The exposure time is a calibration parameter that modifies the luminosity (or the "exposure") of the image. The focal length is a calibration parameter that modifies the viewing angle, i.e. the degree of "zoom". The "sensitivity" is a calibration parameter that modifies the reaction of the sensor of a digital acquisition apparatus to incident light.

Preferably, the calibration parameters are chosen from the group formed by the aperture, the exposure time, the focal length and the sensitivity.

What is meant by an "image" is a two-dimensional image such as a photograph. An image is made up of pixels. The acquired images are extraoral images, i.e. taken from the outside of the patient's mouth.

What is meant by an "updated image" is an image acquired by an image acquisition apparatus. A composite image, according to the first main refinement of the invention, is an example of an updated image.

The term "fasten" means "fix rigidly". The term "fasten" does not necessarily mean "fix definitively". The term "immobilization" includes a fixation which is rigid or not. In particular, an image acquisition apparatus which rests on a support is regarded as immobilized on the support.

The terms "comprise", "include" and "have" should be interpreted broadly and without limitation, unless specified otherwise.

BRIEF DESCRIPTION OF THE FIGURES

Additional features and advantages of the invention will become further apparent upon reading the following detailed description and from studying the attached drawing, in which:

FIGS. 9a, 9b, 9c, 9d, 9e, 9f, 9g and 9h show different views of a kit according to the invention, the device being according to the first improvement. The dental retractor is not represented.

In the various figures, identical or analogous members have been denoted by the same references.

DETAILED DESCRIPTION

Device

Figure 1:
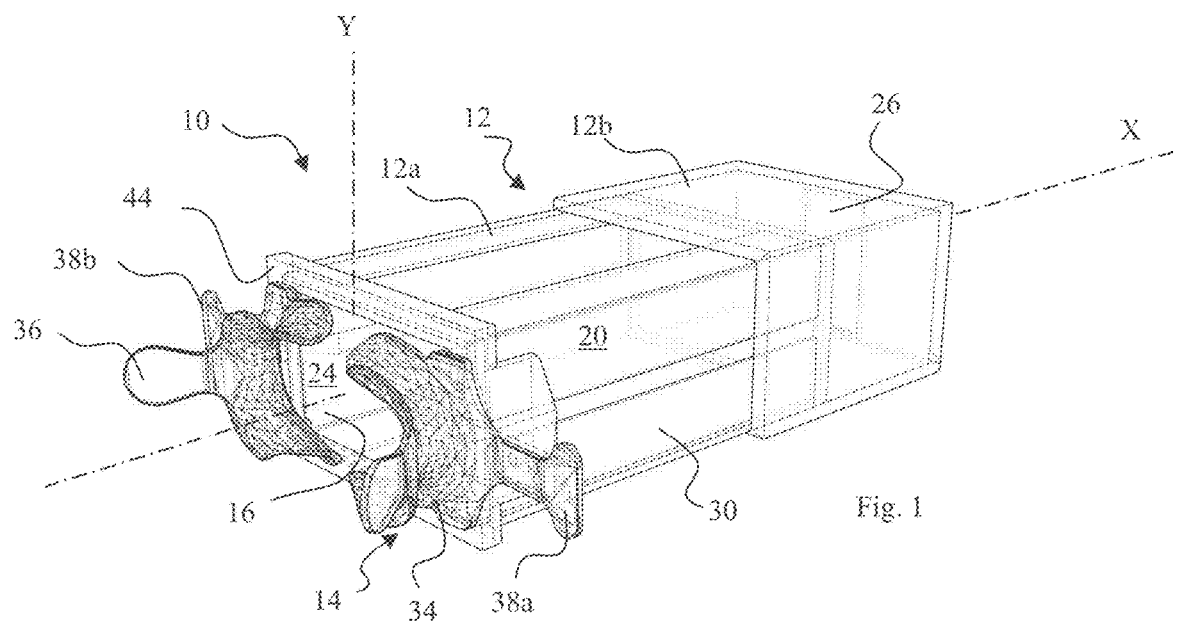
FIG. 1 shows, in perspective, a device according to the invention, seen through the side of the dental retractor.
Figure 2:
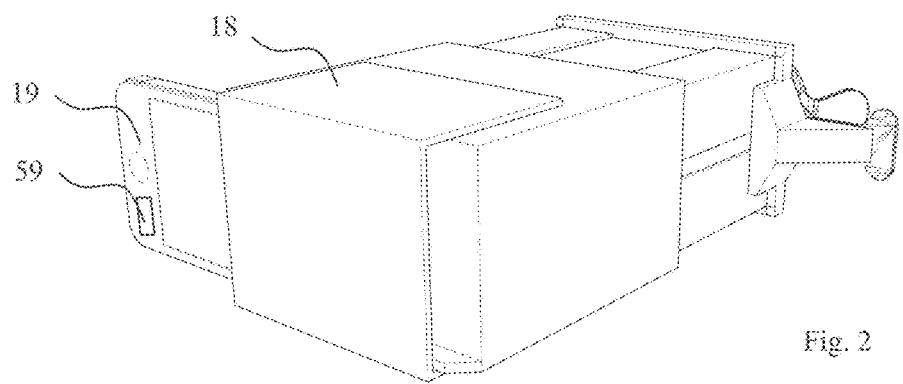
FIG. 2 shows, in perspective, a device according to the invention shown from the acquisition opening side.

The imaging device 10 shown in FIG. 1 includes a support 12, taking the form of an, optionally telescopic, box, a dental retractor 14, preferably at least one mirror 16, and fastening means 18 of an image acquisition apparatus 19, shown in FIG. 2.

In one embodiment, the support 12 includes a male portion 12a and a female portion 12b that are mounted so as to slide one inside the other, along a retractor axis X, between retracted (FIG. 5a) and deployed (FIG. 5b) positions.

In one embodiment, a scale is arranged on the male portion 12a of the support. Preferably, this scale provides indications facilitating the adjustment of the length, along the X axis, of the support 12, for example by bearing a mark for each type of image acquisition apparatus.

The support 12 defines a chamber 20, the length of which along the X axis depends on the relative position of the male and female portions of the support 12 when the box is telescopic, or is constant.

Figure 7:
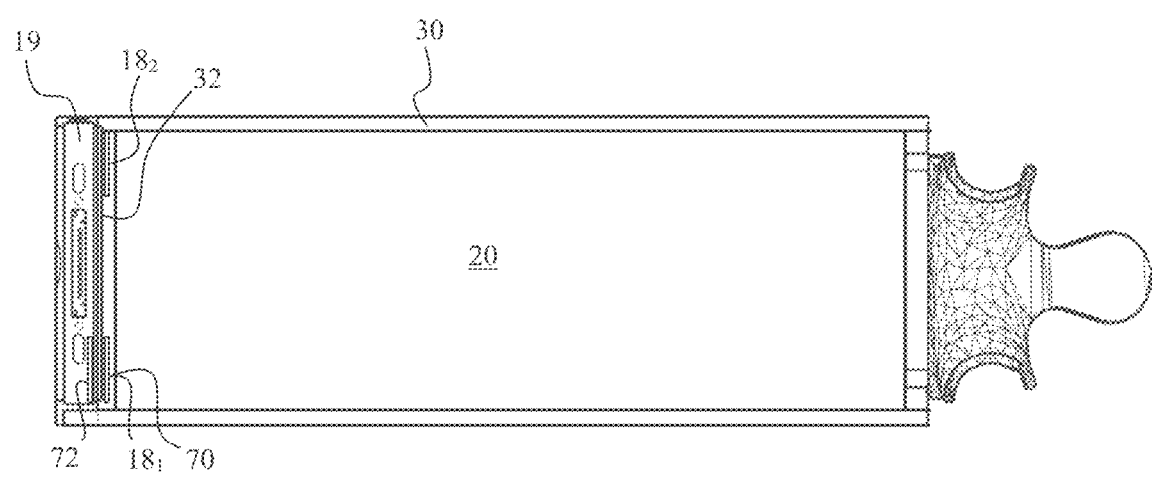
FIG. 7 shows a kit according to the invention comprising a side view of an imaging device according to the invention.

In one preferred embodiment, the box is not telescopic (FIG. 7). When the box is not telescopic, the distance between the retractor and acquisition openings is advantageously constant. The analysis of the updated images is facilitated thereby. Furthermore, this embodiment is advantageously simple, inexpensive and ergonomical.

In the embodiment shown, the chamber 20 is in communication with the outside at two opposite end faces of the support 12, via a retractor opening 24 and an acquisition opening 26, respectively.

The lateral wall 30 of the support 12, which extends between the two end faces, is preferably substantially cylindrical along the X axis, and preferably rectangular in cross section.

In one embodiment, the support 12 is provided with a window through which light from the surroundings may reach inside the chamber 20 in order to illuminate the teeth.

Preferably, however, the chamber 20 is only in communication with the outside via the retractor opening and acquisition opening.

The box thus composed may for example be made of plastic or of a fibrous material, preferably in a cellulosic material such as cardboard.

The fastening means 18 are configured so that the image acquisition apparatus may be fastened in an acquisition position in which its objective faces the acquisition opening 26, or else obturates the acquisition opening 26.

The means 18 for fastening the acquisition apparatus to the support 12 may be of any type. Preferably, they allow rigid fastening. Preferably, they can be reversibly deactivated, i.e. the user may fix the acquisition apparatus to, and dissociate the acquisition apparatus from, the support at will.

Preferably, the fastening means 18 of the acquisition apparatus are chosen from the group consisting of clip-fastening means, self-gripping strips of Velcro® type, clamping jaws, screws, magnets, elastic members, and complementarity of shape between the support and the acquisition apparatus. In the embodiment shown in FIG. 2, the fastening means 18 consist of a cover that may be clamped against the support 12.

In one embodiment, the fastening means 18 of the acquisition apparatus are suitable for fastening a conventional camera, for example of reflex type.

Preferably, as shown in FIG. 7, the means 18 for fastening the acquisition apparatus are magnetic. In particular, one or more magnets $18_1$, $18_2$ may be provided on the support and one or more metal parts may be fastened to the image acquisition device so as to cooperate with the one or more magnets. In particular, a metal plate 32 may be held fast on the image acquisition apparatus, preferably sandwiched between the acquisition apparatus and a protective shell that is fastened to the acquisition apparatus.

In one embodiment, the acquisition apparatus includes multiple metal parts and/or the support includes multiple magnets.

Advantageously, it is therefore sufficient for the operator to bring the acquisition device close to the support for the acquisition apparatus to be fastened to the support. The use of magnetic fastening also allows very precise and reliable fastening, even when the operator is not looking at the support or the acquisition apparatus.

Preferably, the means 18 for fastening the acquisition apparatus, and in particular the one or more magnets and metal parts, are configured so that the acquisition apparatus may be fastened to the support in only one predetermined position. The fastening of the acquisition apparatus therefore requires no particular training for the operator.

Where appropriate, visual guides may be present to guide the operator and to ensure the correct positioning of the acquisition apparatus.

The dental retractor 14 may have the features of conventional retractors. A conventional retractor conventionally includes a rim 34 extending around the retractor opening 24 and arranged in such a way that the patient's lips may rest on it, leaving the patient's teeth visible through said retractor opening. In the embodiment shown, the dental retractor 14 also includes lobes 36 that are arranged so as to spread the cheeks away from the teeth and right 38a and left 38b tabs, which are substantially perpendicular to the X axis, facilitating the handling thereof.

The rim 34 has the shape of a channel configured to hold the patient's lips.

The dental retractor 14 is preferably made of a biocompatible material, for example of a plastic material.

Preferably, the dental retractor is removable, i.e. it may be mounted on and dismounted from the support by the operator. Advantageously, the same support may therefore be used for multiple retractors, and in particular for multiple retractors of different sizes.

The means for fastening 15 the dental retractor to the support may be for example clip-fastening means, self-gripping strips of Velcro® type, clamping jaws, screws, magnets, complementarity of shape between the support and the dental retractor, and elastic members like an elastic band.

In one embodiment, the dental retractor 14 is fastened by means of insertion of one of the right 38a and left 38b tabs into a compartment of the support, then clipping the other tab onto the support.

In one embodiment, the dental retractor 14 is fastened by means of clipping the tabs into respective compartments of the support.

Figure 6A:
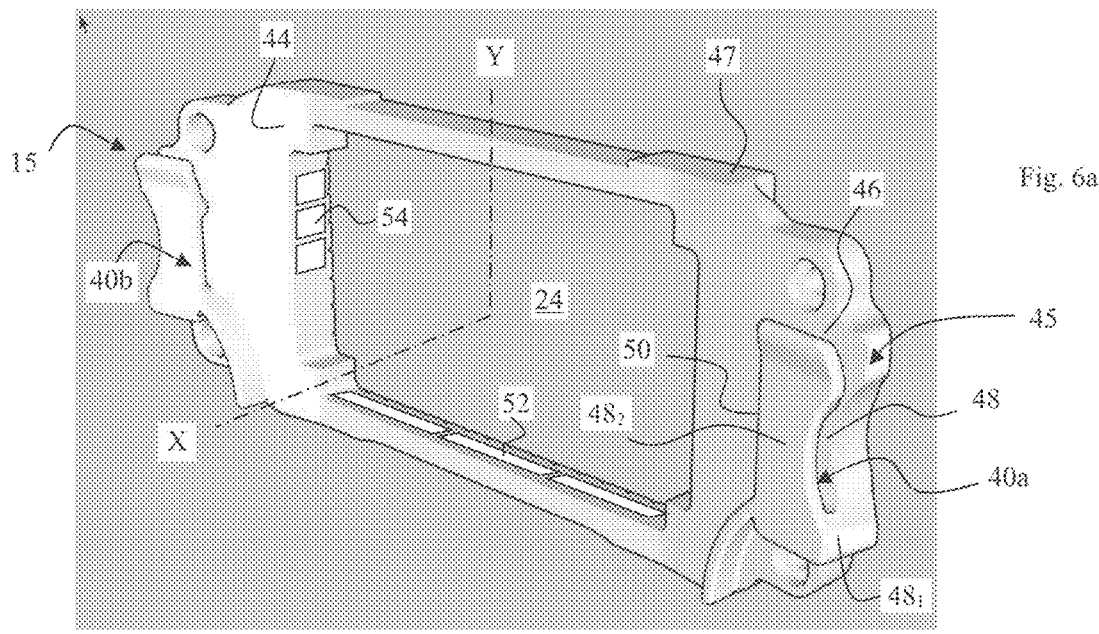
FIGS. 6a, 6b and 6c show, in perspective (FIGS. 6a and 6b) and from above (FIG. 6c), the portion of the support of a device according to the invention on which a dental retractor may be mounted, as shown in FIG. 6b.
Figure 6B:
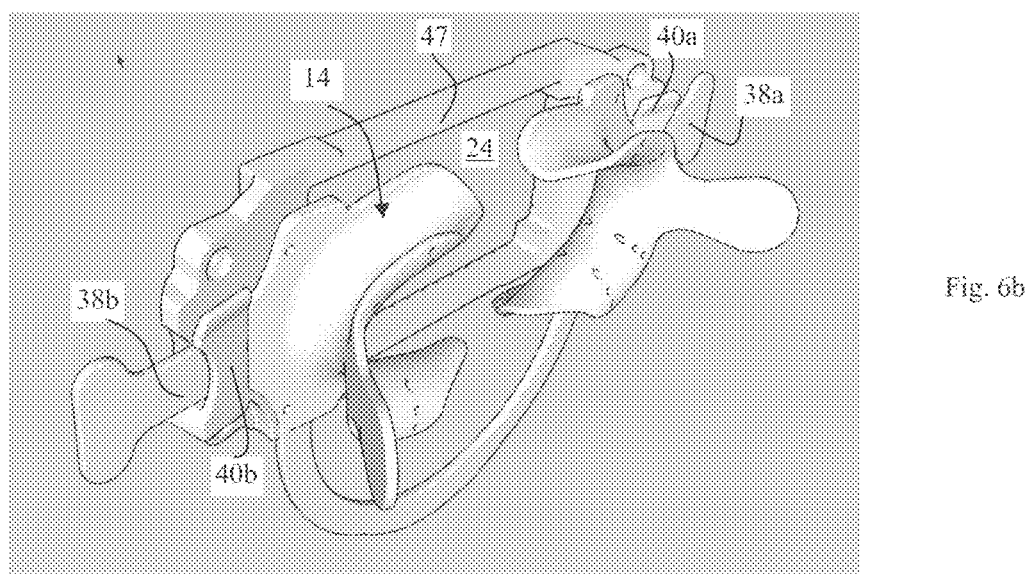

In one preferred embodiment, illustrated by FIG. 6, the means for fastening 15 the dental retractor to the support include a hook onto which the dental retractor 14 may be hooked. The means for fastening 15 the dental retractor to the support preferably include a right hook 40a and a left hook 40b that are arranged so as to accommodate the right 38a and left 38b transverse tabs of the dental retractor, respectively. Since the right and left hooks are similar, only one hook is described in detail below.

Preferably, said hook protrudes from the rear face 44 of the support, substantially perpendicularly to the X axis, as shown in FIG. 1. The rear face 44 is preferably defined by a plate 47 (FIG. 6a) that is fastened to an edge of the lateral wall 30 of the support 12.

Preferably, the hook takes the form of an angle 45. The angle preferably includes first and second wings that are perpendicular to one another. The first wing $48_1$, fastened to the rear face 44 of the support, is preferably substantially parallel to the X axis and the second wing $48_2$ is preferably substantially perpendicular to the X axis and, preferably, extends upward from the first wing. Along with the rear face 44 of the support, the angle 45 defines a compartment with a U-shaped profile, the main, upward-oriented opening 46 of which is sized so as to accommodate a tab of the dental retractor. Again preferably, the profiled compartment is open at its two right and left ends via right 48 and left 50 openings through which a tab of the dental retractor may be slid into the hook, i.e. between the rear face 44 of the support and the second wing $48_2$ of the angle 45, until abutting against the first wing $48_1$.

Preferably, the hooks are configured so that the dental retractor may be inserted therein only by force, preferably by elastically opening the hooks.

Preferably, the hooks are configured so that the dental retractor may be inserted therein without being deformed, preferably by flexing around an axis Y that is substantially perpendicular to the X axis, preferably substantially vertical in the service position.

Again preferably, in the position in which the dental retractor is mounted on the support, fastening means 15 hold the dental retractor flexed around the Y axis.

Figure 6C:
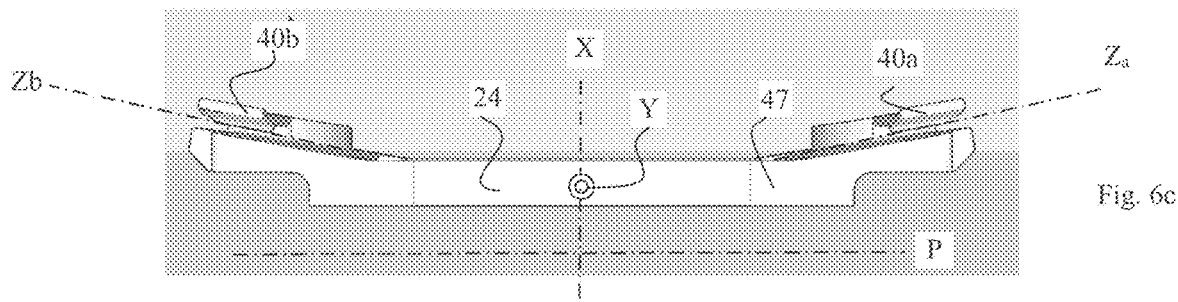

In the embodiment of FIG. 6 (FIG. 6c), the axes $Z_a$ and $Z_b$ of the angles of the left and right hooks are thus inclined with respect to a transverse plane P that is perpendicular to the X axis, while the right and left tabs of the dental retractor are substantially coplanar when the dental retractor is at rest, dissociated from the support. The width of the main openings 46 of the right and left hooks is substantially identical to the thickness of the right and left tabs of the dental retractor, respectively, which obliges the operator to flex the dental retractor around the Y axis in order to insert these tabs into these hooks. The shape of the hooks then prevents the dental retractor from returning to its rest position.

The elastic bearing of the dental retractor on the support thus obtained advantageously favors its being held in position.

The means 15 for fastening the dental retractor are preferably magnets or comprises magnets and metallic inserts cooperating with said magnets. Preferably, the magnets are rigidly fixed to the support and cooperate with metallic inserts rigidly fixed to the dental retractor. The same support may advantageously be used with different retractors, possibly having different sizes, with a limited cost.

Preferably, the dental retractor comprises two magnets or metallic inserts, preferably metallic inserts, preferably made in inox, located on the right and on the left of the retractor opening. Metallic inserts have advantageously a better resistance to high temperatures.

In an embodiment, the dental retractor comprises a magnet in a first location, for instance on the right of the retractor opening, and a metallic insert in another location, for instance on the left of the retractor opening, and the support comprises corresponding metallic insert and magnet. Advantageously, the patient cannot invert the position of the dental retractor, i.e. to put the lower part of the dental retractor above its upper part.

It is also possible to use magnets on the dental retractor and on the support. The magnets are preferably oriented so that the dental retractor may only be fastened to the support in one predetermined position.

In one preferred embodiment, the device includes a light source 51 that is preferably oriented toward the retractor opening 24 (FIG. 5a) so as to illuminate the teeth of the patient through the retractor opening 24. The light source 51 may in particular emit white light, monochromatic light, infrared radiation or, preferably, ultraviolet radiation.

The light source 51 may be a flash.

The light source is preferably fastened to the box. It preferably comprises LEDs.

In one embodiment, the light source 51 is configured so as to project, onto the teeth, through the retractor opening 24, a reference frame, preferably a laser grid. Advantageously, the representation of a reference frame on the images facilitates the determination of the shape of the teeth. A first estimation of the shape of the teeth is thus possible without implementing the method described in PCT/EP2015/074896.

In one embodiment, threading is formed on the lateral wall 30 of the box, preferably on the lateral wall of the female part 12b of the box. The threading is preferably shaped so as to allow the support to be fastened to a camera tripod.

In one embodiment, the device also includes an acquisition cover and a retractor cover, which covers are shaped so as to selectively obturate the acquisition opening and the retractor opening in order to facilitate the storage of the device. Preferably, the retractor cover is shaped so as to selectively obturate the retractor opening after dismounting the retractor.

According to the first main refinement of the invention, the device includes a mirror 16.

The mirror 16 is fastened to the inner face of the lateral wall 30.

The mirror 16 is preferably planar.

The number and the shape of the mirrors are not limiting. In particular, the mirror may be rectangular, spherical, oval, octagonal or hexagonal in shape.

In the embodiment shown, mirrors 16 cover the entire inner face of the lateral wall of the chamber 20, at least in the female portion 12b of the support 12 and, preferably, also in the male portion 12a of the support.

In one embodiment, the device includes four mirrors each positioned on one of the four faces of the lateral wall of the support, and in particular of the female portion 12b and, preferably, of the male portion 12a of the support. In one preferred embodiment, each mirror entirely covers the face of the support 12 over which it extends.

The length of a mirror may be greater than 3 cm, greater than 5 cm and/or smaller than 30 cm, smaller than 20 cm, smaller than 15 cm, or smaller than 10 cm. The width of a mirror may be greater than 2 cm, greater than 3 cm and/or smaller than 10 cm or smaller than 8 cm.

In the embodiment shown, the mirrors are fastened to the support, preferably definitively, for example by means of an adhesive.

The mirror 16, preferably each mirror 16, preferably extends in parallel to the X axis. In the embodiment shown, the mirror 16 extend perpendicularly to one another, pairwise.

The simultaneous presence of a mirror and of a light source 51 is particularly advantageous since it makes it possible to acquire images of the teeth that simultaneously show the reflection of the light source 51 off the teeth, but also the reflection of the fictive light source obtained by reflection of the light source 51 by the mirror. Analyzing the relative position of these reflections in the images advantageously makes it possible to roughly determine the orientation of the surface of the teeth returning them, as well as the position of this surface with respect to the acquisition apparatus.

According to the second main refinement of the invention, the device includes a colorimetric calibration chart 52 and/or a translucence calibration chart 54 that is fastened to the support, preferably in the chamber 20, or to the retractor cover, or to the mouth retractor.

The number and the shape of the calibration charts are not limiting. In one embodiment of FIG. 6a, the support bears for example three colorimetric calibration charts 52 and three translucence calibration charts 54.

Advantageously, the colorimetric 52 and translucence 54 calibration charts make it possible, for each image, to correct hue errors specific to each image acquisition apparatus.

The colorimetric 52 and translucence 54 calibration charts also advantageously make it possible to determine the exact colors and translucence of the teeth or of the gums, thereby allowing any variation in these properties to be detected.

Preferably, the colorimetric 52 and translucence 54 calibration charts are fastened in proximity to the retractor opening, preferably at less than 5 cm, less than 3 cm, less than 1 cm from the retractor opening. Preferably, the colorimetric 52 and translucence 54 calibration charts are fastened substantially in the plane of the retractor opening, as shown in FIG. 6a.

Preferably, the monitoring module 60 monitors the properties of the radiation emitted by the light source 51, preferably as a function of the luminous radiation received by the retractor opening. A light sensor may be provided, in proximity to the retractor opening, for the purpose of evaluating the luminous radiation received by said retractor opening.

In one embodiment, the monitoring module 60 controls the power of the light source 51 so that more than 50%, more than 70%, more than 90%, or even substantially 100% of the intensity of the radiation received by the retractor opening comes from the light source 51.

According to the third main refinement of the invention, the support takes the form of a box that is in communication with the outside substantially only via the retractor and acquisition openings. Advantageously, the influence of the outside environment on the box is limited, thereby allowing images to be acquired under constant conditions. Furthermore, when the device includes a light source 51, a closed box advantageously makes it possible to limit the power of the light source 51.

Preferably, the total area of the openings other than the spacer and acquisition openings represents less than 10%, preferably less than 5%, preferably less than 1% of the area of the lateral wall of the box delimiting the chamber 20. Preferably, the box includes no such "other openings".

In one embodiment, the lateral wall delimiting the chamber 20 is formed or consists of a material that does not allow the content of the chamber 20 to be accurately discerned, including the arches of the patient when the device is in a service position in which a patient has placed his or her lips in the channels of the dental retractor. Advantageously, such a lateral wall specifically completely protects the user's privacy while acquiring the updated images.

In one embodiment, the lateral wall is translucent.

Preferably, the lateral wall is opaque. Advantageously, the inner volume of the chamber receives substantially no light from the outside, thereby guaranteeing constant conditions for acquiring updated images.

According to the first improvement of the invention, the support has a lateral wall defining the chamber, and the lateral wall comprises a rigid portion defining the acquisition opening, and a deformable portion defining the retractor opening.

By "rigid", it is meant that, after the fastening of the image acquisition apparatus, the rigid portion substantially keeps its shape when it is manipulated by an operator to acquire images.

By "deformable", it is meant that the shape of the deformable portion may be substantially modified, preferably without any tool, by the operator, in particular to change the distance between the centre of the acquisition opening and the centre of the retractor opening and/or the angulation of the acquisition opening relatively to the retractor opening.

The deformable portion may in particular be extendable, as according to the second improvement of the invention.

The deformable portion may be used to modify the acquisition conditions for acquiring an image.

The deformable portion may be used to improve the comfort of the patient. In particular, when a conventional retractor is fixed onto a rigid support, its stiffness may lead to a determined shape which does not meet the anatomies of all patients. The deformable portion allows for an adaptation to the anatomy of each patient.

The deformability also enables the fastening of conventional dental retractors having different sizes.

The deformability of the deformable portion may be limited. In particular, the lateral wall in the deformable portion is preferably configured so that it only allows for
  a change of the angulation of the acquisition opening relative to the retractor opening of less than 30°, less than 20°, less than 10° and/or greater than 1°, and/or
  a change of the distance between the centre of acquisition opening and the centre of the retractor opening of less than 5 cm, less than 3 cm, less than 2 cm, less than 1 cm, and/or greater than 0.1 cm.

The deformable portion may in particular be a bellow, in particular a bellow as described previously, or a flexible skirt or a flexible bead.

When the deformable portion is used to improve the comfort of the patient, it is preferably fixed to the dental retractor.

According to the second improvement of the invention, the support, preferably a lateral wall defining a chamber of the support, is extendable, preferably manually, and preferably without any tool, from a collapsed configuration.

A "collapsing" is an operation during which the support, preferably the lateral wall, is made more compact. The collapsing may in particular result in portions of the support, preferably of the lateral wall, being pushed on each other so as to be adjacent to each other.

An "extension" is the opposite operation.

In the collapsed configuration, the device is advantageously more compact. Consequently, the storage and shipment costs are reduced.

In an embodiment, at least one dimension of the support, and in particular of the chamber defined by the lateral wall, has a "collapsed" value $D_c$, in the collapsed configuration, and an "extended" value $D_e$, greater than the collapsed value $D_c$, in a fully extended configuration. Preferably, the ratio $D_c/D_e$ is less than 0.5, preferably less the 0.4, preferably less the 0.3, preferably less the 0.2, preferably less the 0.1.

Preferably, the collapsed value $D_c$ is less than 5 cm, preferably less than 4 cm, preferably less than 3 cm.

Said dimension may be the length, measured along the axis L of the chamber, or the width or the thickness, preferably the length or the width, preferably the length of the chamber.

Of course, the lateral wall may be extendable along several dimensions, for instance along the length and along the width of the support.

Preferably, the lateral wall is also collapsible from the fully extended configuration to the collapsed configuration.

The collapsing may result from the insertion of rigid parts of the lateral wall into each other, in a telescopic way. However, preferably, it results from a deformation of a deformable portion of the lateral wall, preferably from a folding of the lateral wall.

Preferably, the lateral wall comprises predetermined folding lines acting as hinges to modify said dimension. The lateral wall is preferably foldable along its length. The folding lines are preferably extending in at least one transversal plane.

In a preferred embodiment, the lateral wall comprises a bellow, preferably configured to allow an extension, and preferably a collapsing along the axis of the acquisition opening. The bellow preferably comprises more than 1, preferably more than 2, preferably more than 3, preferably more than 4, and/or preferably less than 10, preferably less than 8, preferably less than 7, preferably less than 6 levels.

In an embodiment, the lateral wall comprises an elastic part. Pulling on said elastic part allows for an extension of the lateral wall to modify said dimension.

A "path" is a succession of intermediate configurations of the lateral wall between the collapsed configuration and a fully extended configuration.

Preferably, in a fully extended configuration and/or in an intermediate configuration, preferably in any fully extended configuration and/or in any intermediate configuration, the angulation and/or the distance between the acquisition opening relative to the retractor opening may be different than in the collapsed configuration. Therefore, the modification of the shape of the lateral wall makes it possible modifying the acquisition conditions for acquiring an image.

In an embodiment, the orientation of the retractor opening relative to the acquisition opening may be easily modified, so that images may be acquired with different angulations.

Advantageously, a bellow allows for an extension and a collapsing of the lateral wall, but also provides some flexibility for the acquisition of images. It also provides several fully extended configurations.

Preferably, in a fully extended configuration and/or in an intermediate configuration, preferably in a fully extended configuration and/or in any intermediate configuration, the support has a stable shape, i.e. when the imaging device is hold, only by the dental retractor, by the patient, the retractor opening extending vertically, the lateral wall keeps its shape.

Preferably, in the fully extended configuration and/or in an intermediate configuration, preferably in any fully extended configuration and/or in any intermediate configuration, the support has a stable shape even when it carries a mobile phone at the terminal end of the support defining the acquisition opening. Advantageously, the device is easier to use.

Preferably, the lateral wall is configured so that the angulation of the acquisition opening relative to the retractor opening is limited to remain less than 100°, preferably less than 90°, preferably less than 80°, preferably less than 70°, and/or greater than 10°, preferably greater than 15°, and/or the distance between the centre of acquisition opening and the centre of the retractor opening is limited to remain greater than 5 cm and preferably less than 30 cm, 25 cm or 20 cm. Advantageously, the acquisition conditions for acquiring an image are thereby limited.

In an embodiment, the lateral wall is configured so that the flexibility of the lateral wall depends on its configuration. Put differently, it is more or less difficult to change the shape of the lateral wall, and of the chamber, depending on its configuration. The operator may thereby identify privileged angulation(s) and/or distance(s), i.e. privileged configuration(s) of the lateral wall. The privileged configurations of the lateral wall may in particular correspond to predetermined acquisition conditions for acquiring images, for instance for acquiring images "from the right", "from the left" and "in face" of the patient.

The acquisition of images is advantageously made easier and faster.

In an embodiment, the lateral wall comprises a bellow having a variable thickness so as to define said privileged configurations.

The lateral wall may be extendable along its all length or along a part of its length.

Figure 8A:
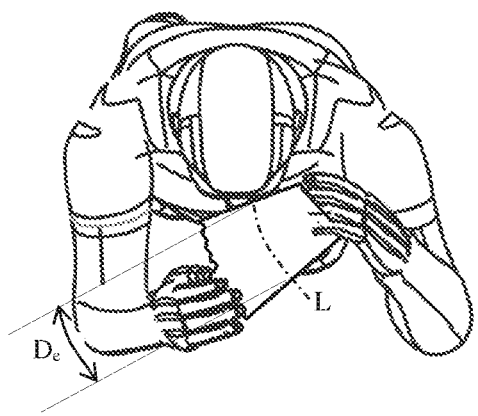
FIGS. 8a and 8b illustrate how a device according to the second improvement may be used.
Figure 8B:
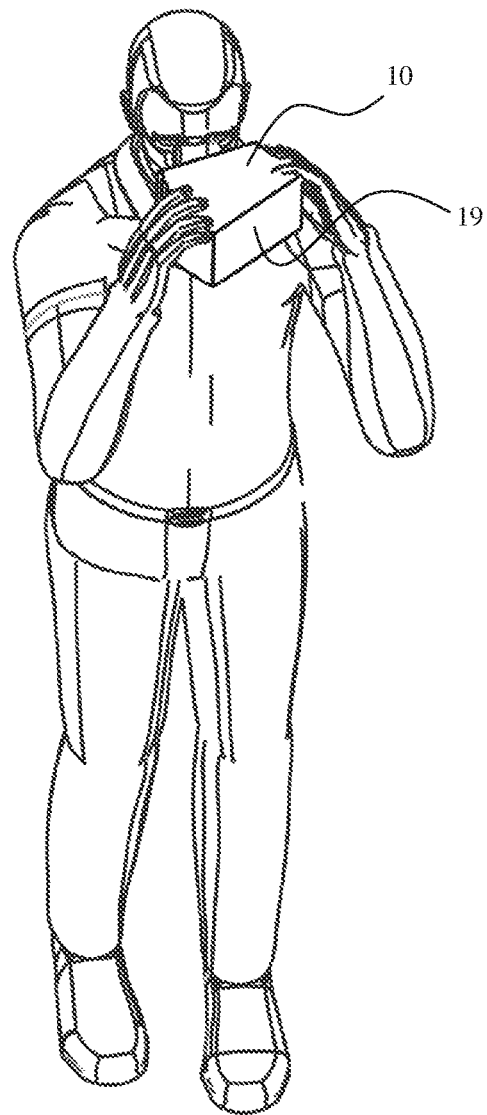

FIGS. 8a and 8b illustrate how a device according to the second improvement may be used.

FIGS. 9a to 9h illustrates an example of a device according to the first and second improvements of the invention.

In this embodiment, the support comprises a rigid portion 64 which defines the acquisition opening 26, and a deformable portion 66 which defines the retractor opening 24.

In an embodiment, the bellow may be pushed inside the rigid proximal part 64, which makes the device more compact and protect the bellows when the device is not used.

The rigid portion 64 comprises a rigid tube 70 and means 18 for fastening the acquisition apparatus to the support 12.

The means 18 for fastening the acquisition apparatus to the support 12 may be of any type. Preferably, they allow rigid fastening. Preferably, they can be reversibly deactivated, i.e. the user may fix the acquisition apparatus to, and dissociate the acquisition apparatus from, the support at will. They may be chosen from the group consisting of clip-fastening means, self-gripping strips of Velcro® type, clamping jaws, screws, magnets, complementarity of shape of the support and of the acquisition apparatus, and elastic members.

In the represented embodiment, they define rails into which the image acquisition apparatus 19, which is here a mobile phone, is inserted, slightly in force. These means could also be a pair of jaws elastically compressing the mobile phone.

Advantageously, the position of the mobile phone along said rails or perpendicular to the compression direction of the jaws can be modified.

The rigidity of the rigid portion makes the fastening of the image acquisition apparatus easier.

The tube 70, having preferably a rectangular cross-section, is similar to the above-described box, but does not define the retractor opening 24. More precisely, it opens to the outside only via the acquisition opening 26, through which the acquisition apparatus fastened to the support receives at least one image of the retractor opening 24. On the side opposite to the acquisition opening, the tube 70 is connected to the collapsible part 66, through a common intermediate opening 72, so that the lateral wall 30 defines a chamber which preferably opens toward the outside only through the retractor opening and the acquisition opening.

The length $L_{70}$ of the tube 70 is preferably greater than 5 cm, and/or less than 20 cm, preferably less than 15 cm, preferably less than 10 cm, so that it may be easily manipulated by the patient.

The deformable portion 66 comprises a bellow 76 and means 15 for fastening a dental retractor to the support 12.

The means 15 are two magnets 78, intended to cooperate with two respective metal inserts rigidly fixed on the dental retractor. Other means 15 are possible, and in particular the fastening means described hereabove for the image acquisition apparatus. Preferably, the means 15 do not allow any substantial modification of the position of the dental retractor once it has been fastened to the support 12.

The bellow 76 has four levels, a level corresponding to a respective folding line 80 on the outside of the bellow 76.

The rigid portion 64 and the deformable portion 66 together define the chamber 20. Laterally, the chamber 20 is delimited by the lateral wall 30 which is partly defined by rigid portion 64 and partly defined by the deformable portion 66.

In a preferred embodiment, at least in the collapsed configuration, the bellow 66 is partly (as represented in the section A-A of FIG. 9g), or completely housed inside the tube 70. The tube advantageously protects the bellows.

In an embodiment, the bellow 76 also defines the acquisition opening. The intermediate opening 72 is then confused with the acquisition opening 26.

The bellow 76 may be rigidly fixed on the rigid portion, in particular along its edge defining the intermediate opening 72. It may also be slidably mounted on the rigid portion, so that it may move along the axis of the tube 70. This embodiment provides protection of the bellow with a maximal extension.

In an embodiment, which is not preferred, the bellow 76 cross the tube 70 and protrudes on both sides of the tube 70. The fixing means 15 and 18 must then be provided on the bellow.

Preferably, the image acquisition apparatus, in particular a mobile phone, has a program to guide the patient toward one or several predetermined acquisition conditions and/or to position the optical axis of the image acquisition apparatus relatively to the retractor opening in a predetermined position. This program preferably uses an artificial neural network.

According to the third improvement, the support, preferably at least a part of the lateral wall, is at least partially, preferably completely in a material which is degradable by composting and/or biodegradation, preferably according to the European standard EN 13432, preferably with a residue of less than 10%, preferably less than 5%, preferably less 1% in 6 months.

Preferably, said material support is in a fibrous material, preferably a cellulosic material is cardboard or paper. The environmental impact of the support is advantageously limited.

Preferably, the support weighs more the 5 g and/or less than 100 g. The impact of its shipping on the environment is therefore limited.

Manufacturing

The manufacture of the support of an imaging device according to the invention, and in particular a device according to the first, second and/or third improvements of the invention, and optionally of the dental retractor, is preferably achieved, from a precursor of said support, in particular when the imaging device is to be manufactured, for instance, less than 1 month, less than 2 weeks, less than 1 week or less than 1 day before being used by the patient.

A "precursor of a support" is a part, or a plurality of parts, or "precursor part(s)", which may be transformed by an operator to get the support.

In an embodiment, the precursor of the support, and optionally of the dental retractor, is (are) manufactured in a first place, and provided to the operator in a second place away from the first place, the distance between the first place and the second place being preferably greater than 1 km and/or less than 20 000 km.

Then, said precursor is transformed into said support, and optionally into said retractor.

The operator is preferably the patient or an orthodontist or a dentist, preferably the patient.

Without precursors, the acquisition of images by the patient normally requires that the patient meets the orthodontist to receive the imaging device, which is not comfortable for the patient. Alternatively, the imaging device may be sent to a patient, but this would generate substantial costs.

In an embodiment, the precursor comprises a precursor part
- the shape of which is to be changed for the manufacturing of the support, in particular by folding and/or bending, and/or
- at least a dimension of which is to be changed for the manufacturing of the support, in particular by cutting, for instance with scissors, or by tearing, and/or
- which needs to be assembled to at least one other part for the manufacturing of the support, in particular by gluing and/or stapling and/or clipping and/or fastening of a loops and hooks fastener of the Velcro® type and/or inserting a tab of the precursor part into a corresponding slot of said other precursor part, or conversely.

The precursor part has preferably a plastic behaviour so that the new shape resulting from said folding and/or bending is stable. Preferably, the new shape is consolidated, for instance by gluing and/or stapling and/or clipping a first region of the precursor part to a second region of the precursor part or of another precursor part, and/or by inserting a tab of said first region into a corresponding slot of said second region.

Preferably, the precursor part bears assembling information to make the manufacturing of the support easier. The assembling information may in particular comprise
- a text, for instance to list the operations required for the manufacturing and/or to provide the number of an hot line, and/or
- visual signs, for instance arrows, warning signs, geometric forms, for instance to indicate emplacements to glue or regions to be assembled together,
- folding lines, i.e. along which the operator is to fold the precursor part, and/or
- tearable weakening lines i.e. along which the operator is to tear the precursor part, and/or
- cutting lines, i.e. along which the operator is to cut the precursor part.

Instructions for the manufacturing are preferably included in a manual, in a numeric form, for instance a video, or a paper form, which is provided to the operator.

The precursor part may in particular have the shape of a sheet. The thickness of the sheet is preferably less than 6 mm, preferably less than 5 mm, preferably less than 4 mm, preferably less than 3 mm, and/or greater than 0.5 mm, preferably greater than 1 mm.

Preferably, the precursor part is in a cellulosic material, preferably in paper or cardboard, in particular when it has the shape of a sheet.

In an embodiment, and in particular when the precursor has the shape of one or several sheets, the precursor is provided to the operator by mail, preferably after being enclosed into an envelope.

To manufacture at least a part of the support from a precursor part having the shape of a sheet, the operator preferably cuts the precursor part along cutting lines, and/or folds the precursor part along folding lines, and/or tears the precursor part along weakening lines, and/or fixes different parts of the precursor part on each other and/or on other precursor parts, by insertion of tabs, or lugs, into corresponding slots or with glue or with staples or with clips or with a loops and hooks fastener of the Velcro® type.

In a preferred embodiment, the support is formed from one or several sheets of cardboard or paper, optionally with glue, preferably without glue, like an origami. These sheets are named "precursor sheets".

In a preferred embodiment, the precursors sheet(s) is (are) also used to form the dental retractor. The dental retractor is preferably integral with the support.

In an embodiment, the precursor comprises one or several sheets of cardboard to be cut by a cutting machine, for instance a laser cutting machine.

The cutting machine may be the property of the operator. The sheets of cardboard may be sent to the operator by mail, or the operator may buy the sheets of cardboard locally.

The cutting machine and the sheets of cardboard may also be available near the location of the operator, for instance in a fabrication laboratory.

The operator is provided, preferably via Internet or with an email, with a file to control a cutting machine to transform said sheets of cardboard into a support. The format of the file is adapted to the cutting machine.

The file and the sheets of cardboard may be loaded in the cutting machine by the operator or by another person. The cutting machine is then operated to manufacture the support or a part of the support, and preferably the dental retractor.

In an embodiment, the precursor comprises a feedstock for a 3D-printer, for instance plastic pellets.

The 3D printer may be the property of the operator. The feedstock may be sent to the operator by mail, or the operator may buy the feedstock locally.

The 3D printer and the feedstock may also be available near the location of the operator, for instance in a fabrication laboratory.

The operator is provided, preferably via Internet or with an email, with a file to control a 3D printer to transform said feedstock into a support. The format of the file is adapted to the printer. It may in particular be the format STL, OBJ, AMF, or 3MF.

The file and the feedstock may be loaded in the 3D printer by the operator or by another person. The 3D printer is then operated to manufacture the support or a part of the support, and preferably the dental retractor.

The following 3D-printing methods are well-known: «SLM®» (Selective Laser Melting), «DMLS» (Direct Metal Laser Sintering), «PS» (Powder Sintering), Infrared sintering, «SLS®» (Selective Laser Sintering), «ALM» (Additive Layer Manufacturing), «CLAD» (Construction Laser Additive Directe), «LFFM» (Laser Free Form Manufacturing), EBM (Electron Beam Melting) from the Swedish company ARCAM, Laser Cusing from the German company Concept Laser, UAM (Manufacturing Additive Ultrasons) or LENS (Laser Engineered Net Shaping).

In an embodiment, parts of the support, and optionally of the dental retractor, are provided to the operator, for instance by the orthodontist, and/or sent to the operator by mail, preferably after being enclosed into an envelope.

Then, the operator assembles said parts, manually or with a tool, optionally with parts that he manufactured himself from a precursor.

In an embodiment, the support or parts of the support having a first shape are provided to the operator, for instance by the orthodontist, and/or sent to the operator by mail, preferably after being enclosed into an envelope.

Then, the operator transforms said support or said parts, manually or with a tool, to give said a second shape. The first shape is preferably more compact than the second shape.

In particular, the first shape may be in a collapsed configuration. The operator may extend the support to a fully extended configuration or to an intermediate configuration.

Imaging Kit

An imaging kit according to the invention includes an imaging device according to the invention and an image acquisition apparatus 19.

The image acquisition apparatus 19 preferably provides color images, and/or infrared images. Infrared images advantageously make it possible to view the teeth with an excellent level of contrast.

Preferably, the image acquisition apparatus 19 is a personal device commonly available on the market, for example a mobile phone, a "connected" camera, a smartwatch, a tablet or a fixed or portable personal computer, including an image acquisition system, such as a webcam or a camera, preferably a digital camera. It preferably weighs less than 3 kg, less than 2 kg, less than 1 kg, less than 500 g, preferably less than 300 g.

The image acquisition apparatus 19 may be integrated within the support 12 or, preferably, be fastened temporarily to the support 12, by virtue of the fastening means 18 of the acquisition apparatus.

In one preferred embodiment, the image acquisition apparatus includes a processing module 59 configured to guide the operator during the imaging operation, in particular so that he or she adjusts the length of the support 12 appropriately and/or so that he or she correctly positions his or her mouth on the dental retractor 14.

Figure 5A:
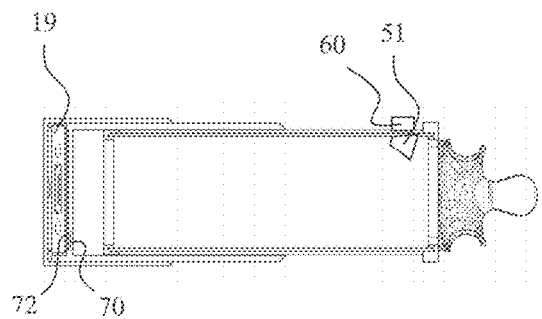
FIGS. 5a and 5b show the device of FIG. 2 with the support in retracted and deployed positions, respectively.
Figure 5B:
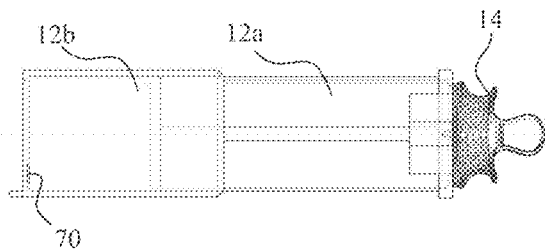

In one preferred embodiment, the imaging device includes a detection member 70 that a detector 72 of the image acquisition apparatus may detect (FIG. 5a).

Preferably, the detection member 70 and the detector 72 are configured so that detection is possible only when the imaging device is in the immediate proximity of the image acquisition apparatus. Advantageously, the image acquisition apparatus therefore does not react when the imaging device is remote therefrom. Preferably however, the detection member 70 and the detector 72 are configured so that the remote detection is possible, preferably at a distance that is greater than 5 cm, or even greater than 10 cm. Advantageously, the image acquisition apparatus may thus react very quickly.

The position of the detection member on the support is not limiting. Preferably however, it is positioned less than 5 cm, preferably less than 3 cm, more preferably less than 2 cm from the edge of the acquisition opening. Advantageously, the acquisition apparatus is thus detected only when the image acquisition apparatus is brought close to the acquisition opening.

In one preferred embodiment, the detection member is a magnet and the detector 72 of the image acquisition apparatus includes a magnetometer. A magnetometer is capable of detecting a change in the magnetic field surrounding it, and is therefore capable of detecting the approach of a magnet.

Since mobile phones are generally provided with a magnetometer, the image acquisition apparatus is preferably a mobile phone.

The detector 72 is configured so as to control the processing module 59, according to the detection of the detection member 70.

In one preferred embodiment, the detector 72 triggers the execution of the computer program loaded on the processing module 59 in the event that the detection member 70 is detected. It is therefore sufficient for the operator to bring the image acquisition apparatus, preferably a phone, close to the support to be guided in his or her image acquisition operations. Such an embodiment advantageously allows an operator who has received no prior training to acquire images.

Preferably, the image acquisition apparatus transmits a message in response to the detection of a detection member 70 by the detector 72. The message preferably relates to the use of the imaging device. Preferably, the image acquisition apparatus is configured to transmit messages relating to the fastening of the acquisition apparatus, for example by means of a voice message saying "place your camera against the blue face of the support", and/or relating to the fastening of the dental retractor, for example by transmitting a voice message saying "bend the dental retractor to fasten it onto the green tabs", and/or relating to the timing of the updated images to be acquired, for example by transmitting a voice message saying "take three photos and send them to your orthodontist".

The message may be purely informative. In one preferred embodiment, the message transmitted by the image acquisition apparatus depends however on the interactions between the operator and the image acquisition apparatus. For example, the image acquisition apparatus may transmit a message saying "the camera is upside down/backwards" or "the camera is not oriented correctly" or "your lips are not correctly positioned in the retractor channel".

The detection member and the detector thus facilitate the acquisition of updated images.

Preferably, the detector 72 and/or the detection member 70 also play a role in fastening the image acquisition apparatus to the support. In particular, the detection member 70 is preferably a magnet 18. The use of a magnet that serves both to detect and to fasten the image acquisition apparatus is advantageously simple, inexpensive and very practical.

Operation

The operation of the kit is directly evident from the description above.

It is described for the embodiment shown in FIG. 7.

Initially, the metal plate 32 is preferably fastened to the image acquisition apparatus 19, in this instance under the protective shell of a mobile phone.

As soon as the operator brings the image acquisition apparatus 19 close to the acquisition opening 26, the metal plate 32 is attracted by the magnets $18_1$ and $18_2$, and cooperates with these magnets to fasten the image acquisition apparatus in a predetermined position, suitable for acquiring updated images according to a predetermined framing. In particular, in this position, the objective of the image acquisition apparatus is correctly positioned with respect to the acquisition opening, preferably substantially in the centre of the acquisition opening, and observes the inside of the chamber 20, in this position, the image acquisition apparatus 19 may observe both the direct image and the reflected image.

Preferably, the mobile phone has a back camera, i.e. a camera on the side of the mobile phone opposite to the display screen of the mobile phone, and it is fastened to the support so that the back camera receives an image of the retractor opening.

The scene which is observed by the back camera therefore appears on the display screen of the mobile phone, which is exposed toward the outside of the device. If the operator is facing a mirror, he can therefore advantageously visualize this scene, and optimize the angulation and/or the distance of the mobile phone to acquire images corresponding to his needs.

Furthermore, on approaching the support, at least one of the magnets $18_1$ and $18_2$ of the support is detected by the magnetometer of the detector 72.

As a result, the magnetometer automatically launches, i.e. without the intervention of the operator, the computer program loaded on the processing module 59 to guide to the operator in his or her operations.

If the box is telescopic, the operator then adjusts the position, along the X axis, of the female portion with respect to the male portion 12a, according to the image acquisition apparatus 19 and its settings.

The scale arranged on the male portion 12a of the support and bearing a mark for each type of image acquisition apparatus facilitates the adjustment.

Preferably, the operator switches on the light source 51 so as to illuminate the teeth and to project the reference frame, in particular a laser grid, on the teeth.

The operator also fastens the dental retractor to the support. In one embodiment shown, he or she inserts a first of the right and left tabs behind a first of the right and left hooks, respectively, then slightly bends the dental retractor in order to allow the second tab to be inserted behind the second hook. When the operator releases his or her action, the dental retractor attempts to return to its initial shape, but this return to the initial shape is hindered by the hooks. The pressure of the dental retractor on the support thus obtained ensures that the dental retractor is held in position behind the hooks.

Preferably, the processing module 59 is configured to control the automatic acquisition of one or more updated images and analyze them to detect any incorrect positioning of the image acquisition apparatus and/or of the dental retractor and/or poor illumination and/or an unsuitable support length. More preferably, the image acquisition apparatus immediately informs the operator thereof so that he or she corrects the detected defects.

A device according to the invention thus makes it possible to provide a predetermined positioning of the image acquisition apparatus with respect to the spread opening, and therefore facilitates the acquisition of updated images. It allows high-quality updated images to be obtained, in particular images that are substantially identical in size, framed in the same way and suitably sharp. The invention therefore facilitates the later analysis of the updated images.

Figure 3:
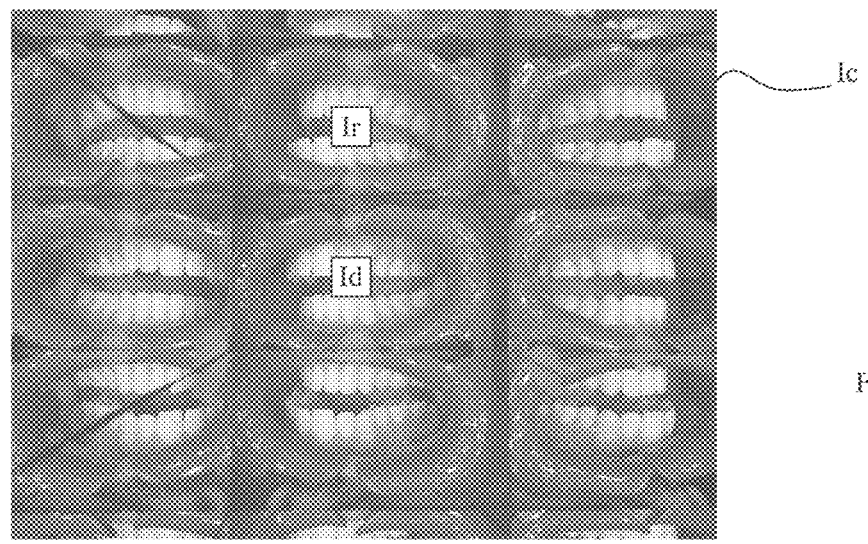
FIG. 3 shows an example of a composite image.
Figure 4A:
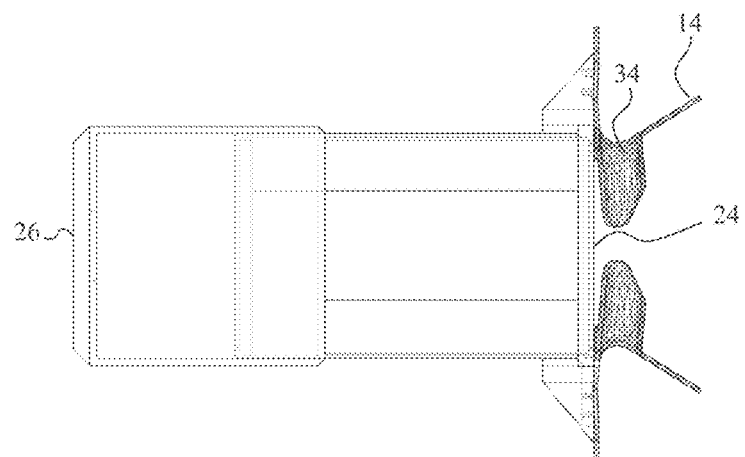
FIGS. 4a, 4b and 4c show the device of FIG. 1 seen from above, seen from the acquisition opening side and seen from the retractor opening side, respectively.
Figure 4B:
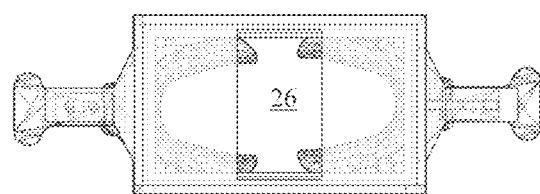
Figure 4C:
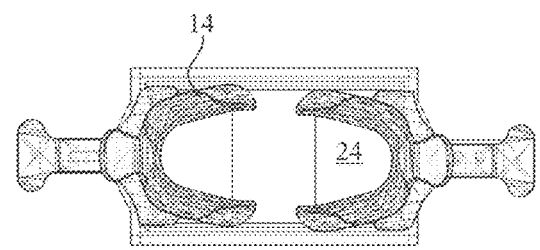

The patient, who may also be the operator, then places his or her lips in the channels defined by the rim 34 of the dental retractor. As shown in FIG. 3, the teeth of the patient are then clearly visible. The closed box advantageously masks the teeth, thereby protecting the patient's privacy.

The device is then in a service position and the image acquisition apparatus 19 views a composite image $I_c$ of the type of that shown in FIG. 3. In this figure, the composite image includes a direct image $I_d$ and eight reflected images $I_r$ reflected by the various mirrors 16 positioned in the chamber 20.

By actuating the trigger of the acquisition apparatus, the operator acquires the composite image $I_c$. Advantageously, he or she simultaneously acquires, like in the embodiment of FIG. 3, a front view (direct image $I_d$) and a set of oblique views (reflected images $I_r$). Of course, the reflected images are inverted with respect to reality. For example, in the reflected image located above the direct image $I_d$, the upper arch is shown below the lower arch.

The reflected images may advantageously correspond to acquisition conditions in which the optical axis of the acquisition apparatus is strongly inclined with respect to the sagittal plane. Using the acquisition apparatus under these conditions, with direct observation, i.e. without a mirror, would often be difficult for the patient.

The composite image is next transmitted to the processing module 59, by wired or wireless means, for example by Wi-Fi or by Bluetooth®.

Image processing makes it possible in particular, according to conventional processing methods, to isolate the direct image and the one or more reflected images. In one embodiment, the processing operation also includes an operation of inverting the reflected images and/or an operation of correcting perspective effects and/or an operation of correcting colours by means of the colorimetric calibration chart 34.

Analyzing one of the direct and reflected images, preferably the direct image, makes it possible to determine the acquisition conditions of said image, preferably according to the teaching of PCT/EP2015/074896, incorporated by reference. The acquisition conditions of the other images may advantageously be deduced therefrom, simply by taking the geometry of the support 12 into account. In particular, the calibration of the acquisition apparatus is the same for all of the direct and reflected images. Additionally, simple geometric considerations make it possible to determine the position and the orientation of the acquisition apparatus in space which, in the absence of a minor, would have allowed the acquisition apparatus to acquire a reflected image.

In one embodiment, the processing module 59, preferably integrated within the image acquisition apparatus 19, controls the acquisition of multiple composite images under different acquisition conditions, and in particular with different focal lengths. For example, first, second and third composite images may be acquired by successively focusing the acquisition apparatus on the incisors, on the premolars and on the molars. Advantageously, each tooth is thus shown clearly in at least one of the composite images.

In one embodiment, taking multiple successive images under different acquisition conditions is the result of a single actuation of the trigger of the image acquisition apparatus.

In particular, the image acquisition apparatus may be configured to take multiple photographs in succession, with different focal lengths, as a result of a single trigger action.

Furthermore, the acquisition apparatus preferably acquires an image of the teeth of the patient also showing the translucence and colorimetric calibration charts.

The processing module 59, having knowledge of the real color and translucence properties of the calibration charts, then corrects the image until the representations of said calibration charts in the image have these properties.

In order to make the correction accurate, the light source 51 is preferably adjusted so that, at the time of acquisition of the image, the calibration charts are illuminated under the same conditions as when measuring the real properties. Using a closed box makes it easier to control the illumination.

All of the images acquired by the acquisition apparatus are thus advantageously comparable, regardless of the lighting environment outside the device at the moment of their acquisition.

As is now clearly apparent, the invention significantly facilitates the analysis of the updated images.

A device according to the first main refinement advantageously makes it possible to acquire multiple images very quickly, typically in less than a minute, without recourse to a specialist, in particular to a dentist or an orthodontist. The images may in particular be acquired by the patient him- or herself or by one of his or her kin, using a simple mobile phone, anywhere, and in particular outside of any medical, dental or orthodontics practice.

In addition, if the geometry of the support, and in particular the orientation and the positioning of a mirror, is known, it is enough to determine the acquisition conditions of the direct image in order to be able to determine, by way of simple calculation, the acquisition conditions of the image reflected by this mirror. The implementation of the method described in PCT/EP2015/074896 is considerably accelerated as a result.

Lastly, since the acquisition apparatus 19 is immobile with respect to the teeth, the composite image is advantageously clear and, if the device includes a controlled light source, exhibits good contrast.

A device according to the second main refinement makes it possible to track variation in the properties of the appearance of the teeth. It also makes it possible for the patient him- or herself to accurately measure these properties at any time, and in particular shortly before a prosthesis is produced, for example. The appearance of the prosthesis is thus particularly close to that of the teeth of the patient.

A device according to the third main refinement facilitates the control of the illumination during the acquisition of updated images and allows the patient's privacy to be protected.

A kit according to the invention substantially facilitates the use of an imaging device according to the invention. In particular, it makes it possible, in one preferred embodiment, to automatically guide the user in his or her operations. The quality of the updated images is advantageously improved thereby.

Of course, the invention is not restricted to the embodiments described and shown, which are provided for illustrative purposes only.

In particular, the shape of the box is not limiting.

Furthermore, although this embodiment is not preferred, the fastening of the image acquisition apparatus may employ one or more magnets that are fastened to the image acquisition apparatus and one or more metal parts that are fastened to the support.

The metal parts of the means for fastening the image acquisition apparatus may also be replaced, at least partially, with magnets that are arranged so as to attract the magnets fastened to the support.

The mirror is not necessarily planar. It may in particular be configured to compensate for perspective effects and/or to reflect particular regions of the mouth.

The mirror may be movable with respect to the support, and in particular may be translatably movable, in particular to make it possible to modify the distance between the mirror and the retractor opening and/or the acquisition opening.

The mirror may also be rotatably movable, in particular about an axis of rotation that is perpendicular to the X axis of the dental retractor, two axes being referred to as perpendicular when two planes that are orthogonal to these axes are perpendicular to one another.

Preferably, the image acquisition apparatus includes an app configured to guide the operator so that he or she correctly positions and orients the minor. In one embodiment, the positioning and/or the orientation of the mirror are facilitated by a scale bearing indications relating to various acquisition apparatuses. The operator may thus easily position the mirror according to the acquisition apparatus used.

In one embodiment, the device includes one or more actuators that are suitable for adjusting the length of the support and/or the positioning and/or the orientation of the mirror according to setpoints, preferably according to setpoints received from the image acquisition apparatus 19.

In one embodiment, the device also includes one or more sensors configured to measure the length of the support 12 and/or the positioning and/or the orientation of the mirror, and a transmitter capable of transmitting said measurement to the image acquisition apparatus. Advantageously, the device may be optimally configured by controlling the actuators according to a setpoint, preferably provided by the image acquisition apparatus, said setpoint preferably being based on the image observed by the image acquisition apparatus and/or by the measurements taken by the sensors.

In addition, the number of mirrors is not limited and multiple mirrors, preferably all of the mirrors, preferably have one or more of the preferred features of the mirror 16 described above. In particular, one or more of the mirrors may be provided with a sensor, with an actuator and with means for communicating with the image acquisition apparatus, as described above.

The invention claimed is:

1. A patient-operated imaging device comprising:
    a support;
    a mouth retractor formed as an integral part of the support and defining a retractor opening; and
    a mechanism for fastening an image acquisition apparatus to the support in a position in which the acquisition apparatus is oriented so as to receive an image of the retractor opening through which, in a service position, front teeth of the patient are visible,
    wherein the support takes the form of a box that is in communication with the outside via the retractor opening and via an acquisition opening through which the image acquisition apparatus fastened to the support receives the image of the retractor opening, the support being configured so that the image acquisition apparatus observes the retractor opening regardless of the configuration of the support;
    the mechanism being chosen from the group consisting of an elastic member, clip-fastening means, self-gripping strips of hook and loop fastener type, clamping jaws, screws, magnets, and complementarity of shape between the support and the image acquisition apparatus, or consisting of a cover that may be clamped against the support,
    wherein the patient-operated imaging device is adapted to obtain a plurality of images, wherein at least two of the plurality of images correspond to different angles with respect to the patient's teeth.

2. The patient-operated imaging device as claimed in claim 1, in which the mechanism is magnetic and configured so that the image acquisition apparatus may be fastened to the support in only one predetermined position.

3. An imaging kit comprising:
    the patient-operated imaging device as claimed in claim 1, and
    an image acquisition apparatus that is fastened to the patient-operated imaging device in a position in which the image acquisition apparatus is oriented to receive an image of the retractor opening.

4. The imaging kit as claimed in claim 3, in which the patient-operated imaging device further comprises a detection member and the image acquisition apparatus further comprises a detector that is configured to detect the detection member when the detection member is less than 20 cm from the patient-operated imaging device.

5. The imaging kit as claimed in claim 4, in which the detector is configured so as to detect the detection member only when the detection member is less than 20 cm from the patient-operated imaging device.

6. The imaging kit as claimed in claim 4, in which the detection member is positioned less than 5 cm from the edge of the acquisition opening.

7. The imaging kit as claimed in claim 4, in which the detector further comprises a magnetometer.

8. The imaging kit as claimed in claim 4, in which the detector is configured to trigger an execution of a computer program loaded on a processing module of the image acquisition apparatus in the event that the detection member is detected.

9. The imaging kit as claimed in claim 8, in which the processing module is configured to acquire, in response to the detection of the detection member by the detector, one or more updated images, then analyze the one or more updated images to detect an incorrect positioning of the image acquisition apparatus and/or an incorrect positioning of the retractor and/or a poor illumination of the retractor opening and/or an unsuitable support length.

10. The imaging kit as claimed in claim 4, in which the image acquisition apparatus transmits a message in response to the detection of the detection member by the detector, the message relating to the use of the patient-operated imaging device and/or relating to the fastening of the acquisition apparatus and/or relating to the fastening of the dental retractor and/or relating to the timing of the updated images to be acquired.

11. The patient-operated imaging device as claimed in claim 1, in which the mechanism for fastening includes the detection member.

12. The patient-operated imaging device as claimed in claim 1, in which the support defines a closed chamber when the opening of the mouth retractor and the acquisition opening are obturated.

13. The patient-operated imaging device as claimed in claim 12, in which a lateral wall delimiting the chamber is formed or consists of a material that does not allow the content of the chamber to be accurately discerned.

14. The patient-operated imaging device as claimed in claim 13, in which the lateral wall is opaque, so that an inner volume of the chamber receives no light from outside of the chamber in a service position.

15. The patient-operated imaging device as claimed in claim 1, in which the mouth retractor comprises lobes that are arranged so as to spread cheeks of a patient away from teeth of the patient.

16. The patient-operated imaging device as claimed in claim 1, further comprising a light source that is oriented toward the retractor opening so as to illuminate teeth of a patient through the retractor opening.

17. The patient-operated imaging device as claimed in claim 16, in which the light source is configured so as to project, through the retractor opening, a reference frame onto the teeth.

18. The patient-operated imaging device as claimed in claim 17, further comprising a monitoring module configured to monitor properties of radiation emitted by the light source as a function of the luminous radiation received by the retractor opening.

19. The patient-operated imaging device as claimed in claim 1, in which the image acquisition apparatus has an objective and is positioned with respect to the acquisition opening so that the objective is maintained in the center of the acquisition opening.

20. The patient-operated imaging device as claimed in claim 1, in which the mechanism is an elastic member.

21. The patient-operated imaging device as claimed in claim 1, in which the rectractor opening is configured so that both teeth of an upper dental arch of the patient and teeth of an lower arch of the patient are fully visible by the image acquisition apparatus.

22. The patient-operated imaging device as claimed in claim 1, in which the support has a lateral wall which extends between two end faces of the support defining the retractor opening and the acquisition opening, respectively, said lateral wall being rectangular in cross section.

23. The patient-operated imaging device as claimed in claim 1, in which the mechanism for fastening the acquisition apparatus is configured so that the acquisition apparatus may be fastened to the support in only one predetermined position.

24. The patient-operated imaging device as claimed in claim 1, in which the retractor includes a rim extending around the retractor opening and arranged in such a way that the patient's lips may rest on it, leaving the patient's teeth visible through said retractor opening.

25. The patient-operated imaging device as claimed in claim 24, in which the rim has the shape of a channel configured to hold the patient's lips.

26. The patient-operated imaging device as claimed in claim 1, in which the retractor opening is curved around an axis Y which is vertical in a service position.

27. The patient-operated imaging device as claimed in claim 1, in which the retractor opening is larger than the acquisition opening.

28. An patient-operated imaging device comprising:
a support;
a mouth retractor formed as an integral part of the support and defining a retractor opening; and
an image acquisition apparatus fastened to the support in a position in which the image acquisition apparatus is oriented so as to receive an image of the retractor opening, through which, in a service position, front teeth of the patient are visible;
wherein the support takes the form of a box that is in communication with the outside via the retractor opening and via an acquisition opening through which the image acquisition apparatus fastened to the support receives the image of the retractor opening, the support being configured so that the image acquisition apparatus observes the retractor opening regardless of the configuration of the support,
wherein the patient-operated imaging device is adapted to obtain a plurality of images, wherein at least two of the plurality of images correspond to different angles with respect to the patient's teeth.

* * * * *